US 6,191,118 B1

(12) United States Patent
Asaka et al.

(10) Patent No.: US 6,191,118 B1
(45) Date of Patent: Feb. 20, 2001

(54) ERYTHROMYCIN A DERIVATIVES

(75) Inventors: Toshifumi Asaka, Konosu; Masato Kashimura, Omiya; Akiko Matsuura, Tokorozawa; Tomohiro Sugimoto, Omiya; Tetsuya Tanikawa, Fuchu; Takaaki Ishii, Urawa, all of (JP)

(73) Assignee: Taisho Pharmaceutical Co., Ltd. (JP)

( * ) Notice: Under 35 U.S.C. 154(b), the term of this patent shall be extended for 0 days.

(21) Appl. No.: 09/297,183

(22) PCT Filed: Oct. 14, 1997

(86) PCT No.: PCT/JP97/03687

§ 371 Date: Apr. 23, 1999

§ 102(e) Date: Apr. 23, 1999

(87) PCT Pub. No.: WO98/23628

PCT Pub. Date: Jun. 4, 1998

(30) Foreign Application Priority Data

Nov. 27, 1996 (JP) .................................... 8-315805

(51) Int. Cl.⁷ .......................... A61K 31/70; C07H 17/08
(52) U.S. Cl. ................................. 514/29; 536/7.4
(58) Field of Search ................... 536/7.4; 514/29

(56) References Cited

U.S. PATENT DOCUMENTS

| 4,331,803 | 5/1982 | Watanabe et al. | 536/7.2 |
|---|---|---|---|
| 4,742,049 | 5/1988 | Baker et al. | 514/29 |
| 5,523,399 | 6/1996 | Asaka et al. | 536/7.3 |
| 5,631,354 | 5/1997 | Asaka et al. | 536/7.4 |
| 5,631,355 | 5/1997 | Asaka et al. | 536/7.4 |

FOREIGN PATENT DOCUMENTS 638584 4/1993 (EP) .

Primary Examiner—John Kight
Assistant Examiner—Raymond Covington
(74) Attorney, Agent, or Firm—Lorusso & Loud

(57) ABSTRACT

An erythromycin A derivative represented by Formula

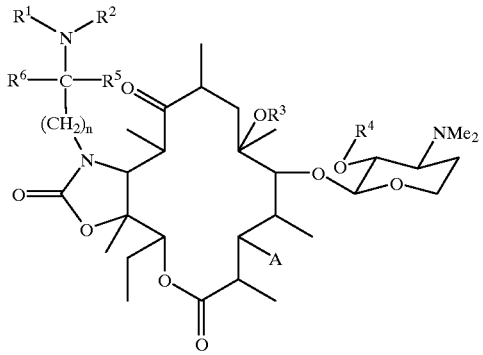

(I)

wherein $R^1$ is a group represented by the formula:

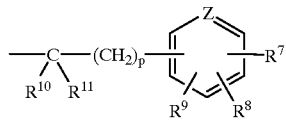

(a)

a group represented by the formula:

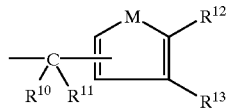

(b)

(c) pyridylacetyl, (d) cycloalkylmethyl or (e) 1,2 bis-(ethoxycarbonyl)vinyl, $R^2$ is the same group as defined for $R^1$, hydrogen, alkyl, alkanoyl, alkoxycarbonyl, $R^1$ and $R^2$ together may form $=CH-R^{14}$, or $R^1$ and $R^2$ together with the nitrogen atom to which they are attached may form:

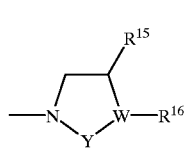

(f)

$R^3$ is hydrogen, alkyl or cinnamyl, $R^4$ is hydrogen, acetyl, ethylsuccinyl or nicotinoyl, A is $-OC(=O)-R^{17}$, $-OC(=O)-CH_2-R^{17}$, $-OC(=O)-NH-R^{17}$, $-O-R^{17}$ or $-OC(=O)-O-R^{17}$, and $R^5$ and $R^6$ are each hydrogen or alkyl.

4 Claims, No Drawings

ERYTHROMYCIN A DERIVATIVES

TECHNICAL FIELD

The present invention relates to novel derivatives of antibiotic erythromycin A.

BACKGROUND ART

Erythromycin A is an antibiotic clinically widely used as an agent for treating infectious diseases caused by Gram-positive bacteria, mycoplasmas, etc. However, erythromycin A is decomposed by the gastric acid due to instability to acids, and thus have a drawback of no constancy of movement in the body. Hitherto many erythromycin A derivatives have been prepared for the purpose of the improvement of the biological or pharmacological properties. For example, it is reported that 6-O-methylerythromycin A derivatives have an improved stability to acids and have a superior in vivo antibacterial activity in comparison with erythromycin A when administered orally (U.S. Pat. No. 4,331,803). There are also recent reports relating to 11,12-cyclic carbamate derivatives prepared from 6-O-methylerythromycin A as a starting material with the aim of expansion of antibacterial spectrum as well as a stability to acids (EP. patent No. 487411 and U.S. Pat. No. 4,742,049). In addition, the present inventors refer to the antibacterial activity of the ester derivatives at the 3-position (EP. Patent No. 619320).

An object of the present invention is to provide a novel antibiotic erythromycin A derivative or a salt thereof having a strong antibacterial activity against not only known erythromycin-sensitive bacteria but also erythromycin-resistant bacteria which recently are showing a tendency to increase, and a composition comprising the same as an effective component.

Other objects of the present invention are to provide a method for the treatment of a bacterially infectious disease which comprises administering a pharmaceutically effective amount of the above-mentioned erythromycin A derivative or a salt thereof to patients, and use of the above-mentioned erythromycin A derivative or a salt thereof for the treatment of a bacterially infectious disease.

DISCLOSURE OF THE INVENTION

As a result of various researches on the antibacterial activity of erythromycin A derivatives, the present inventors have found that, among 6-O-methylerythromycin A 11,12-cyclic carbamate derivatives, in particular, the derivatives which are substituted by a substituted aminoalkyl group on the nitrogen atom forming the cyclic carbamate ring and converted into an ester at the 3-position have a strong antibacterial activity against erythromycin-resistant bacteria, and have further studied about analog compounds thereof, whereby the present invention has been accomplished.

The present invention relates to an eythromycin A derivative represented by Formula (I):

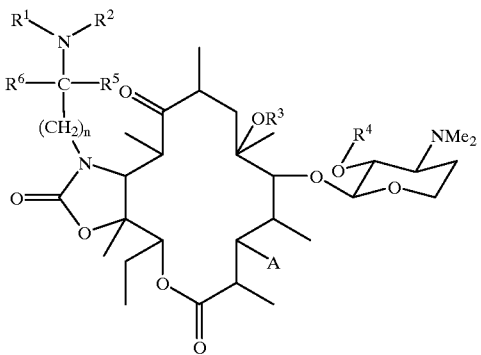

[wherein n is an integer of from 1 to 4,
R$^1$ is a group represented by the formula:

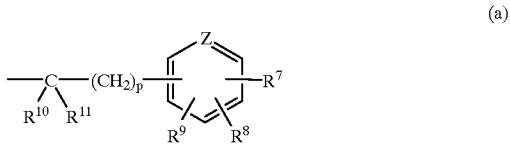

(wherein p is 0 or 1, Z is a nitrogen atom or CH; R$^7$, R$^8$ and R$^9$ are each a hydrogen atom, a halogen atom, an alkyl group having 1 to 5 carbon atoms, a nitro group, an amino group, an acetylamino group, an amino group substituted by 1 or 2 alkyl groups having 1 to 3 carbon atoms, a hydroxyl group, a cyano group, an alkyl group having 1 to 3 carbon atoms substituted by 1 to 3 halogen atoms, an alkoxy group having 1 to 5 carbon atoms or a phenyl group, or R$^7$ and R$^8$ are attached to the carbon atoms which are attached side by side, and together form a methylenedioxy group, or R$^7$ and R$^8$ are attached to the carbon atoms which are attached side by side, and together with the carbon atoms to which they are attached form a benzene ring, R$^{10}$ and R$^{11}$ are each a hydrogen atom, or R$^{10}$ and R$^{11}$ together form an oxo group), a group represented by the formula:

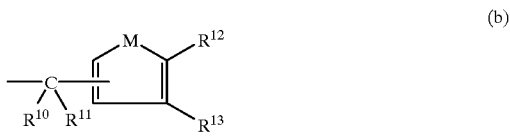

(wherein R$^{10}$ and R$^{11}$ are as defined above, M is an oxygen atom, a sulfur atom, —NCH$_3$ or —NH, or R$^{12}$ and R$^{13}$ are each a hydrogen atom, or R$^{12}$ and R$^{13}$ together with the carbon atoms to which they are attached form a benzene ring), a pyridylacetyl group, a cycloalkylmethyl group having 4 to 8 carbon atoms or a 1,2-bis(ethoxycarbonyl)vinyl group, R$^2$ is the same group as defined for R$^1$, a hydrogen atom, an alkyl group having 1 to 5 carbon atoms, an alkanoyl group having 2 to 6 carbon atoms or an alkoxycarbonyl group having 2 to 6 carbon atoms, R$^1$ and R$^2$ together form a group of the formula: =CH—R$^{14}$ (wherein R$^{14}$ is a phenyl group, a phenyl group substituted by nitro group(s), cyano group(s) or alkyl group(s) having 1 to 3 carbon atoms substituted by 1 to 3 halogen atoms, or an imidazolyl group), or R$^1$ and R$^2$ together with the nitrogen atom to which they are attached form a group represented by the formula:

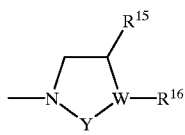

(c)

(wherein W is CH, a carbon atom or a nitrogen atom, Y is a group of —C(=O)— or —(CH$_2$)$_m$— (wherein m is 1 or 2), R$^{15}$ and R$^{16}$ are each a hydrogen atom or when W is a carbon atom, R$^{15}$ and R$^{16}$ together with the carbon atoms to which they are attached form a benzene ring or a naphthalene ring, R$^3$ is a hydrogen atom, an alkyl group having 1 to 5 carbon atoms or a cinnamyl group, R$^4$ is a hydrogen atom, an acetyl group, an ethylsuccinyl group or a nicotinoyl group, A is a group represented by the formula:

—OC(=O)—R$^{17}$,

—OC(=O)—CH$_2$—R$^{17}$,

—OC(=O)—NH—R$^{17}$,

—O—R$^{17}$ or

—OC(=O)—O—R$^{17}$ (wherein R$^{17}$ is a phenyl group, a pyridyl group, a quinolyl group, or those groups which are each substituted by 1 to 3 members selected by the group consisting of an alkyl group having 1 to 5 carbon atoms, a nitro group, an alkoxy group having 1 to 5 carbon atoms and a halogen atom), and R$^5$ and R$^6$ are each a hydrogen atom or an alkyl group having 1 to 5 carbon atoms] or a pharmaceutically acceptable salt thereof.

In the present invention, the alkyl group having 1 to 5 carbon atoms refers to a straight or branched chain alkyl group, for example, a methyl group, an ethyl group, a propyl group, an isopropyl group, a butyl group, a tert-butyl group or a pentyl group. The alkoxy group having 1 to 5 carbon atoms refers to a straight or branched chain alkoxy group, preferably a methoxy group or an ethoxy group. The halogen atom refers to a fluorine atom, a chlorine atom, a bromine atom or an iodine atom. Examples of the 6-membered ring and the condensed ring in the group represented by Formula (a) are a benzene ring, a naphthalene ring, a pyridine ring, a quinoline ring and an isoquinoline ring. Examples of the 5-membered ring and the condensed ring in the group represented by Formula (b) are a furan ring, a thiophene ring, a pyrrole ring, a benzofuran ring, a benzothiophene ring and an indole ring. Examples of the 5-membered ring, the 6-membered ring and the condensed ring in the group represented by Formula (c) are a pyrrolidine ring, a piperidine ring, an imidazolidine ring, an isoindoline ring, a 1,2,3,4-tetrahydroisoquinoline ring and a 2-oxoisoindoline ring.

The amino group substituted by 1 or 2 alkyl groups having 1 to 3 carbon atoms as defined for R$^7$, R$^8$ and R$^9$ is preferably an amino group substituted by methyl group(s), more preferably a dimethylamino group.

The alkyl group having 1 to 3 carbon atoms substituted by 1 to 3 halogen atoms as defined for R$^7$, R$^8$, R$^9$ and R$^{14}$ is preferably an alkyl group substituted by fluorine atom(s), more preferably a methyl group substituted by fluorine atom(s), and most preferably a trifluoromethyl group.

The pharmaceutically acceptable salt refers to a salt used in chemotherapy or prophylaxis of bacterially infectious diseases, for example, a salt with acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanic acid, polyacrylate or carboxyvinyl polymer.

The compounds of the present invention can be prepared, for example, by the following methods, but not limited thereto.

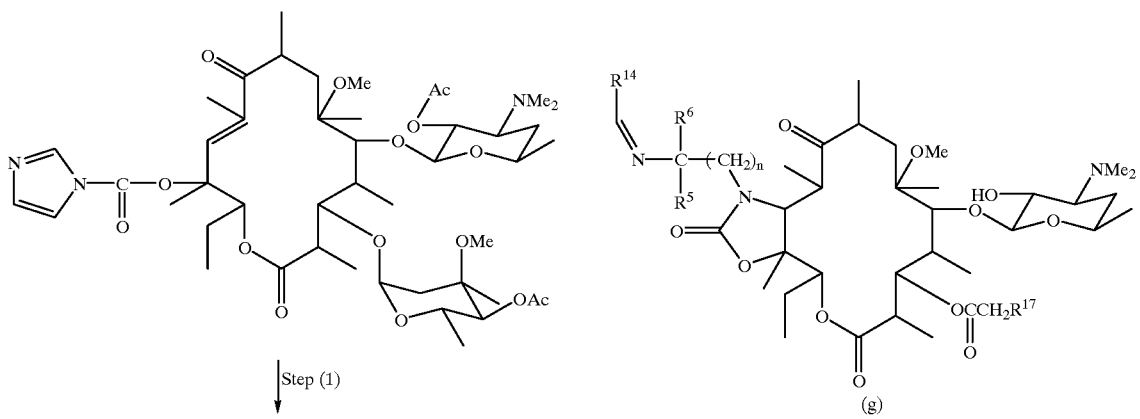

-continued
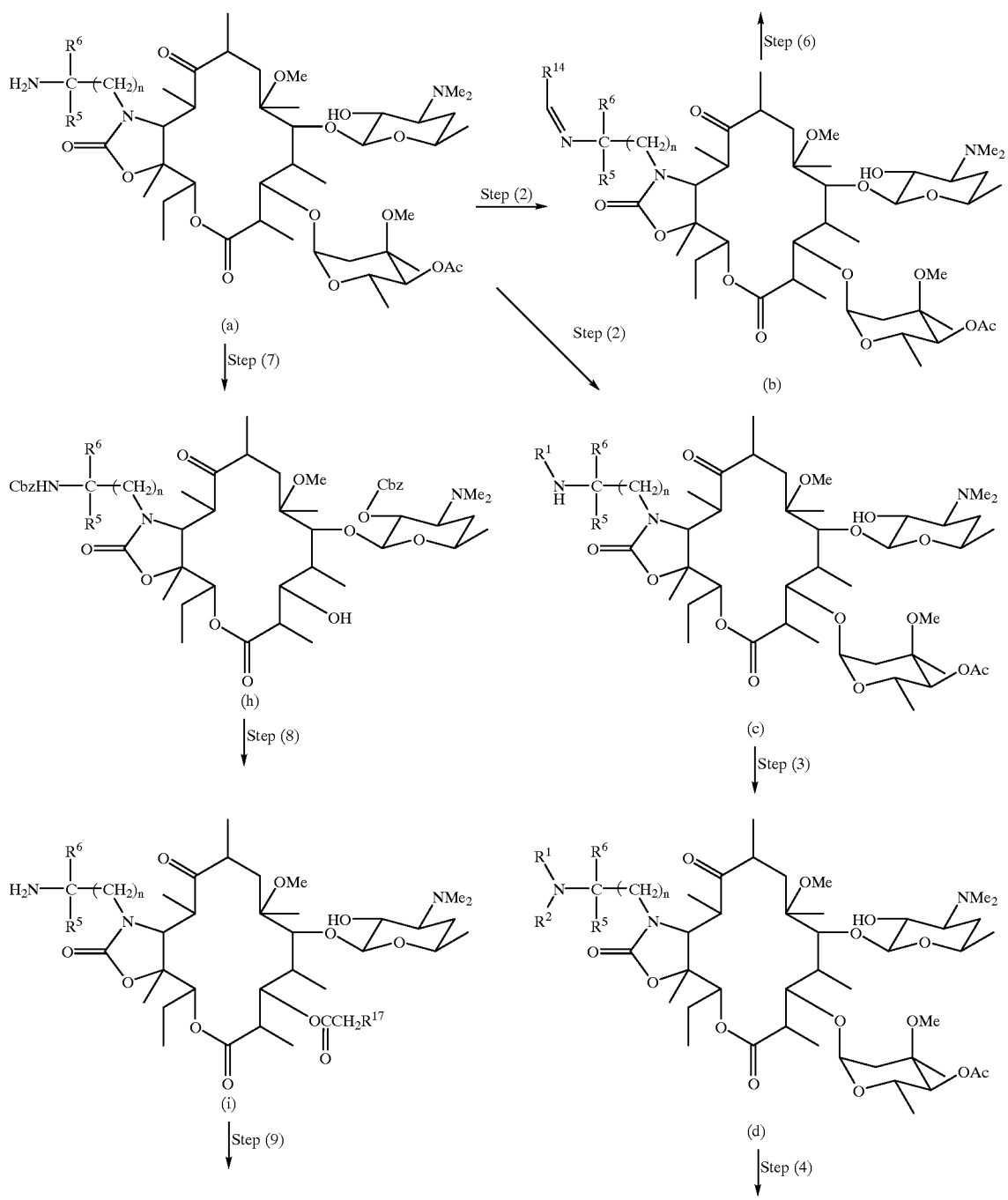

-continued

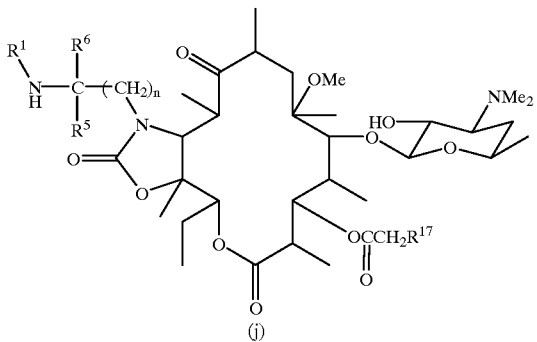

(j)

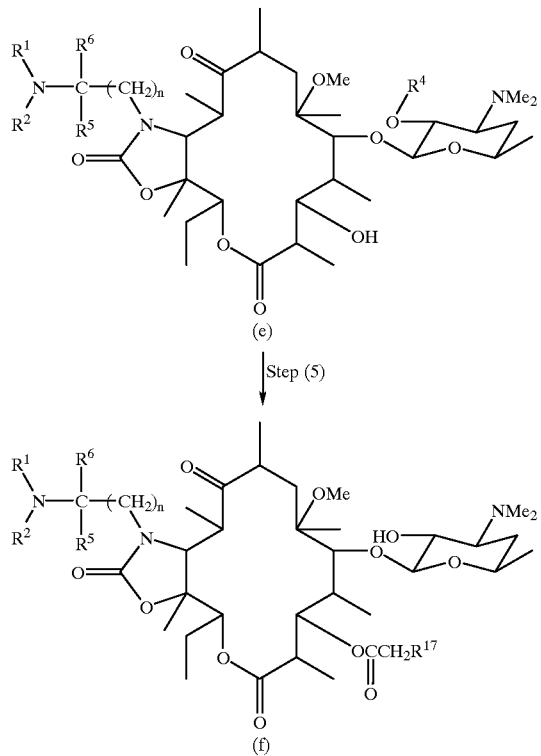

(e)

Step (5)

(f)

Step (1); 10,11-Anhydro-2',4"-di-O-acetyl-12-O-imidazolylcarbonyl-6-O-methylerythromycin A described in EP patent No. 638584 is reacted with an agent represented by the formula:

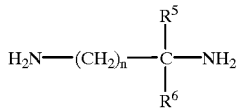

(wherein, $R^5$, $R^6$ and n are as defined above) in an inert solvent at a temperature of from −30° C. to 100° C. The resulting 11,12-cyclic carbamate compound is reacted in a lower alcohol or an aqueous lower alcohol, if desired, in the presence of a base such as sodium bicarbonate, at a temperature of from 0° C. to 100° C. to remove the protective group at the 2'-position, and whereby there is obtained a compound of Formula (a) (wherein $R^5$, $R^6$ and n are as defined above). Examples of the inert solvent to be used herein are acetonitrile, tetrahydrofuran, N,N-dimethylformamide, dioxane, ethyl acetate, N-methylpyrrolidone, an aqueous solution thereof and a mixture thereof. Examples of the lower alcohol to be used herein are methanol, ethanol and propyl alcohol.

Step (2); The compound of Formula (a) is reacted with a slight excess amount of an aldehyde compound (e.g. pyridylaldehyde) relative to the compound of Formula (a) in a lower alcohol in the presence of an acid such as acetic acid at a temperature of from −30° C. to 60° C. to give a compound of Formula (b) (wherein $R^5$, $R^6$, $R^{14}$ and n are as defined above). When the reaction is carried out, addition of a reductant in the system gives a compound of Formula (c) (wherein $R^1$, $R^5$, $R^6$ and n are as defined above). The lower alcohol is the same as used in Step (1). Examples of the reductant to be used herein are sodium borohydride, sodium cyanoborohydride and sodium triacetoxyborohydride.

Step (3); The compound of Formula (c) is reacted in the same manner as in Step (2) using formaldehyde, acetaldehyde, quinolylaldehyde, furaldehyde, thiophenecarboxaldehyde or pyridylaldehyde to give a compound of Formula (d) (wherein $R^1$, $R^2$, $R^5$, $R^6$ and n are as defined above).

Step (4); The compound of Formula (d) is reacted with an acid such as hydrochloric acid for removal of the sugar at the 3-position, and then protected with, for example, an acetyl group at the 2'-position in an ordinary manner to give a compound of Formula (e) (wherein $R^1$, $R^2$, $R^4$, $R^5$, $R^6$ and n are as defined above).

Step (5); The compound of Formula (e) is reacted using a reagent represented by the formula:

$R^{17}$—

(wherein $R^{17}$ is as defined above) and an activating agent thereof in an inert solvent in the presence of a base such as 4-dimethylaminopyridine at a temperature of from −30° C. to 30° C. to give a 3-ester compound, which is then subjected to the same deprotection at the 2'-position as in Step (1) in a lower alcohol or an aqueous lower alcohol to give a compound of Formula (f) which is a compound of the present invention. Examples of the activating agent to be used herein are 1,3-dicyclohexylcarbodiimide, 1-(3-dimethylaminopropyl)-3-ethylcarbodiimide hydrochloride and pivaloyl chloride. Examples of the inert solvent to be used are dichloromethane, dichloroethane, acetone, pyridine, ethyl acetate and tetrahydrofuran.

Step (6); The compound of Formula (b) is treated in the same manners as in Step (4) and Step (5), successively, to give a compound of Formula (g) (wherein $R^5$, $R^6$, $R^{14}$, $R^{17}$ and n are as defined above).

Step (7); The compound of Formula (a) is treated in the same manner as in Step (4) for removal of the sugar at the 3-position, and then the primary amino group and the hydroxyl group at the 2'-position are protected with benzyloxycarbonyl groups in an ordinary manner to give a compound of Formula (h) (wherein $R^5$, $R^6$ and n are as defined above).

Step (8); The compound of Formula (h) is treated in the same manner as in Step (5) for esterification at the 3-position, and then the benzyloxycarbonyl groups are removed by an ordinary manner such as catalytic hydrogenolysis to give a compound of Formula (i).

Step (9); The compound of Formula (i) is reacted with an acid halide in an inert solvent in the presence of a base such as pyridine or 4-dimethylaminopyridine to give a compound of Formula (j) (wherein $R^1$, $R^5$, $R^6$, $R^{17}$ and n are as defined above) which is a compound of the present invention. The inert solvent herein is the same as used in Step (5), and examples of the acid halide are benzoyl chloride, nicotinoyl chloride and quinolinoyl chloride.

The compounds of the present invention can be administered orally or parenterally in the various preparation forms for the purpose of the application based on the pharmacological properties. The pharmaceutical composition of the present invention can be prepared by homogeneously mixing an effective amount of the compound of the present invention in the free form or in the form of an acid addition salt thereof, with a pharmaceutically acceptable carrier, which may be various forms according to the desired dosage forms. Examples of the dosage forms in the present invention are tablets, capsules, powders, troches, ointments, suspensions, suppositories and injections, all of which can be prepared according to conventional preparation techniques.

The dose of the compound of the present invention to adults is from 100 to 1000 mg/day in 2 or 3 divided doses. This dose can be increased or decreased depending on the age, body weight and conditions of the patient.

BEST MODE FOR CARRYING OUT THE INVENTION

The present invention is illustrated in more detail by the following Examples.

EXAMPLE 1

Synthesis of 11-{2-[N,N-bis(3-pyridylmethyl)amino] ethyl}amino-11-deoxy-3-O-(3-pyridyl)acetyl-5-O-desosaminyl-6-O-methylerythronolide A 11,12-cyclic carbamate (1) To a solution of 70.0 g (77 mmoles) of 10,11-anhydro-2',4"-di-O-acetyl-12-O-imidazolylcarbonyl-6-O-methylerythromycin A described in European Patent No. 638584 in 1 L of acetonitrile was added 30.0 ml (231 mmoles) of ethylenediamine at room temperature, followed by stirring overnight. The reaction solution was evaporated under reduced pressure and dissolved in 1 L of methanol, followed by heating under reflux for 4 hours. After evaporation of the solvent, purification by silica gel column chromatography (chloroform:methanol:aqueous ammonia= 20:1:0.1) gave 67.0 g (yield: 97%) of the 11-(2-aminoethyl) amine compound.

(2) To a solution of 5.0 g (6.0 mmoles) of the compound obtained in the above (1) in 60 ml of methanol were added 2.8 ml (30 mmoles) of nicotinealdehyde and 3.9 ml (61 mmoles) of acetic acid, then 1.9 g (30 mmoles) of sodium cyanoborohydride under ice-cooling. The reaction solution was heated to 60° C. under reflux for 4 hours.

The reaction solution was adjusted to pH 10 with 4N sodium hydroxide, and extracted with chloroform. The organic layer was dried over anhydrous magnesium sulfate, followed by evaporation of the solvent under reduced pressure. The residue was purified by silica gel column chromatography (chloroform:methanol:aqueous ammonia= 20:1:0.1) to give 2.3 g (yield: 38%) of the 11-{2-[N,N-bis (3-pyridylmethyl)amino]ethyl}amino compound, a solution of which in 30 ml of 1N aqueous hydrochloric acid solution was stirred at room temperature overnight. After the reaction, the mixture was made basic with 4N aqueous sodium hydroxide solution, and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 1.7 g (yield: 87%) of the 3-hydroxyl compound.

(3) To a solution of 1.7 g (2.0 mmoles) of the compound obtained in the above (2) in 20 ml of methylene chloride was added 0.35 ml (3.1 mmoles) of acetic anhydride at room temperature, followed by stirring overnight. The reaction solution was made basic with a saturated aqueous sodium bicarbonate solution and extracted with chloroform. The chloroform layer was washed with distilled water and an aqueous sodium chloride solution. The organic layer was dried over anhydrous magnesium sulfate, followed by evaporation of the solvent under reduced pressure to give 1.7 g of the 2'-O-acetyl compound.

(4) To a solution of 0.50 g (0.57 mmole) of the compound obtained in the above (3) in 10 ml of methylene chloride were successively added 0.20 g (1.1 mmoles) of 3-pyridylacetic acid hydrochloride, 0.21 g (1.1 mmoles) of 1-(3-dimethylaminopropyl)-3-ethylcarbodiimide hydrochloride and 0.05 g (0.41 mmole) of 4-dimethylaminopyridine under ice-cooling, followed by stirring at room temperature for 1.5 hours. The reaction solution was made basic with 2N sodium hydroxide and extracted with chloroform. The organic layer was dried over anhydrous magnesium sulfate, followed by evaporation of the solvent under reduced pressure. The residue was dissolved in 14 ml of methanol, and heated under reflux for 2 hours. After evaporation of the solvent, purification by silica gel column chromatography (chloroform:methanol:aqueous ammonia=20:1:0.1) gave 0.30 g (yield: 55%) of the title compound.

Mass (FAB; 3-NBA) m/z: 959 [M+H]$^+$; $^1$H-NMR (500 MHz, CDCl$_3$) δ(ppm): 0.77 (t, 3H, J=7.3 Hz, H15), 2.27(s, 6H, NMe$_2$), 2.83 (s, 3H, 6-OMe), 4.99 (d, 1H, J=11.0 Hz, H3), 5.01 (m, 1H, H13).

EXAMPLE 2

Synthesis of 11-{2-[N,N-bis(3-pyridylmethyl)amino] ethyl}amino-11-deoxy-3-O-(2-pyridyl)acetyl-5-O-desosaminyl-6-O-methylerythronolide A 11,12-cyclic carbamate To a solution of 0.41 g (0.47 mmole) of the compound obtained in Example 1(3) in 10 ml of methylene chloride were successively added 0.16 g (0.93 mmole) of 2-pyridylacetic acid hydrochloride, 0.18 g (0.93 mmole) of 1-(3-dimethylaminopropyl)-3-ethylcarbodiimide hydrochloride and 0.05 g (0.41 mmole) of 4-dimethylaminopyridine under ice-cooling, followed by stirring at room temperature for 1.5 hours. The reaction solution was made basic with 2N sodium hydroxide and extracted with chloroform. The organic layer was dried over anhydrous magnesium sulfate, followed by evaporation of the solvent under reduced pressure. The residue was dissolved in 10 ml of methanol, and heated under reflux for 2 hours. After evaporation of the solvent, purification by silica gel column chromatography (chloroform:methanol:aqueous ammonia=20:1:0.1) gave 0.30 g (yield: 66%) of the title compound.

Mass (FAB; 3-NBA) m/z: 959 [M+H]$^+$; $^1$H-NMR (500 MHz, CDCl$_3$) δ(ppm): 0.77 (t, 3H, J=7.3 Hz, H15), 2.29 (s, 6H, NMe$_2$), 2.84 (s, 3H, 6-OMe), 5.00 (d, 1H, J=11.6 Hz, H3), 5.01 (dd, 1H, J=11.0, 2.4 Hz, H13).

EXAMPLE 3

Synthesis of 11-{2-[N-methyl-N-(3-pyridylmethyl)amino]ethyl}amino-11-deoxy-3-O-(3-pyridyl)acetyl-5-O-desosaminyl-6-O-methylerythronolide A 11,12-cyclic carbamate (1) To a solution of 20.0 g (22.4 mmoles) of the compound obtained in Example 1(1) in 200 ml of methanol were added 2.8 ml (29.1 mmoles) of nicotinealdehyde and 7.3 ml (112 mmoles) of acetic acid, then 2.8 g (44.8 mmoles) of sodium cyanoborohydride under ice-cooling. The temperature was turned to room temperature, followed by stirring for 4 hours. The reaction solution was made basic with 4N sodium hydroxide and extracted with diethyl ether. The organic layer was dried over anhydrous magnesium sulfate, followed by evaporation of the solvent under reduced pressure. The residue was dissolved in 200 ml of ethanol, and then 30.0 ml (224 mmoles) of 37% aqueous formaldehyde solution and 11.0 ml (224 mmoles) of 90% aqueous formic acid solution were added thereto, followed by heating under reflux for 3.5 hours. The reaction solution was evaporated under reduced pressure, made basic with 4N sodium hydroxide and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 21.0 g (yield: 97%) of the 11-{2-[N-methyl-N-(3-pyridylmethyl)amino]ethyl}amino compound.

(2) A solution of the compound obtained in the above (1) in 200 ml of 1N aqueous hydrochloric acid solution was stirred at room temperature overnight, made basic with 4N aqueous sodium hydroxide solution, and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 13.0 g (yield: 82%) of the 3-hydroxyl compound.

(3) Following the same procedure as in Example 1(3) using 13.0 g (17.1 mmoles) of the compound obtained in the above (2), there was obtained 12.7 g of the 2'-O-acetyl compound.

(4) Following the same procedure as in Example 1(4) using 0.25 g (0.31 mmole) of the compound obtained in the above (3), there was obtained 0.15 g (yield: 55%) of the title compound.

Mass (FAB; 3-NBA) m/z: 882 [M+H]$^+$; $^1$H-NMR (500 MHz, CDCl$_3$) δ(ppm): 0.71 (t, 3H, J=7.32 Hz, H15), 2.18 (s, 3H), 2.28 (s, 6H, NMe$_2$), 3.02 (s, 3H, 6-OMe), 5.04 (d, 1H, J=11.0 Hz, H3), 5.18 (dd, 1H, J=11.0, 2.4 Hz, H13).

EXAMPLE 4

Synthesis of 11-{2-[N-methyl-N-(3-pyridylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 2 using 0.31 g (0.39 mmole) of the compound obtained in Example 3(3), there was obtained 0.25 g (yield: 73%) of the title compound.

Mass (FAB; 3-NBA) m/z: 882 [M+H]$^+$; $^1$H-NMR (500 MHz, CDCl$_3$) δ(ppm): 0.72 (t, 3H, J=7.32 Hz, H15), 2.19 (s, 3H), 2.29 (s, 6H, NMe$_2$), 3.02 (s, 3H, 6-OMe), 5.06 (d, 1H, J=11.0 Hz, H3), 5.19 (dd, 1H, J=11.0, 2.4 Hz, H13).

EXAMPLE 5

Synthesis of 11-{2-[N,N-bis(2-pyridylmethyl)amino]ethyl}amino-11-deoxy-3-O-(3-pyridyl)acetyl-5-O-desosaminyl-6-O-methylerythronolide A 11,12-cyclic carbamate (1) Following the same procedure as in Example 1(2) using 2.08 g (2.5 mmoles) of the compound obtained in Example 1(1) and 0.47 ml (5.0 mmoles) of 2-pyridinecarboxaldehyde, there was obtained 0.90 g (yield: 43%) of the 3-hydroxyl compound.

(2) Following the same procedure as in Example 1(3) using 0.77 g (0.92 mmole) of the compound obtained in the above (1), there was obtained 0.80 g (yield: 99%) of the 2'-O-acetyl compound.

(3) Following the same procedure as in Example 1(4) using 0.39 g (0.44 mmole) of the compound obtained in the above (2), there was obtained 0.23 g (yield: 55%) of the title compound.

Mass (FAB; 3-NBA) m/z: 959 [M+H]$^+$; $^1$H-NMR (500 MHz, CDCl$_3$) δ(ppm); 0.73 (t, 3H, J=7.32 Hz, H15), 2.27 (s, 6H, NMe$_2$), 2.86 (s, 3H, 6-OMe), 4.99 (d, 1H, J=11.6 Hz, H3), 5.01 (dd, 1H, J=11.0, 2.4 Hz, H13).

EXAMPLE 6

Synthesis of 11-{2-[N,N-bis(2-pyridylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 2 using 0.40 g (0.44 mmole) of the compound obtained in Example 5(2), there was obtained 0.40 g (yield: 79%) of the title compound.

Mass (FAB; 3-NBA) m/z: 959 [M+H]$^+$; $^1$H-NMR (500 MHz, CDCl$_3$) δ(ppm): 0.73 (t, 3H, J=7.32 Hz, H15), 2.29 (s, 6H, NMe$_2$), 2.85 (s, 3H, 6-OMe), 5.00 (d, 1H, J=11.6 Hz, H3), 5.01 (dd, 1H, J=11.0, 2.4 Hz, H13).

EXAMPLE 7

Synthesis of 11-{2-[N-methyl-N-(2-pyridylmethyl)amino]ethyl}amino-11-deoxy-3-O-(3-pyridyl)acetyl-5-O-desosaminyl-6-O-methylerythronolide A 11,12-cyclic carbamate (1) Following the same procedure as in Example 3(1) using 0.34 ml (3.6 mmoles) of 2-pyridinecarboxaldehyde in place of nicotinealdehyde and 3.00 g (3.6 mmoles) of the compound obtained in Example 1(1), there was obtained 1.43 g (yield: 41%) of the 11-{2-[N-methyl-N-(2-pyridylmethyl)amino]ethyl}amino compound.

(2) Following the same procedure as in Example 3(2) using 1.40 g (1.46 imoles) of the compound obtained in the above (1), there was obtained 1.03 g (yield: 93%) of the 3-hydroxyl compound.

(3) Following the same procedure as in Example 1(3) using 0.88 g (1.20 mmoles) of the compound obtained in the above (2), there was obtained 0.83 g (yield: 97%) of the 2'-O-acetyl compound.

(4) Following the same procedure as in Example 1(4) using 0.35 g (0.44 mmole) of the compound obtained in the above (3), there was obtained 0.33 g (yield: 85%) of the title compound.

Mass (FAB; 3-NBA) m/z: 882 [M+H]$^+$; $^1$H-NMR (500 MHz, CDCl$_3$) δ(ppm): 0.68 (t, 3H, J=7.32 Hz, H15), 2.27 (s, 3H), 2.30 (s, 6H, NMe$_2$), 3.02 (s, 3H, 6-OMe), 5.03 (d, 1H, J=11.0 Hz, H3), 5.17 (dd, 1H, J=11.0, 2.4 Hz, H13).

EXAMPLE 8

Synthesis of 11-{2-[N-methyl-N-(2-pyridylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 2 using 0.35 g (0.44 mmole) of the compound obtained in Example 7(3), there was obtained 0.30 g (yield: 77%) of the title compound.

Mass (FAB; 3-NBA) m/z: 882 [M+H]$^+$; $^1$H-NMR (500 MHz, CDCl$_3$) δ(ppm): 0.69 (t, 3H, J=7.32 Hz, H15), 2.27 (s, 3H), 2.29 (s, 6H, NMe$_2$), 3.02 (s, 3H, 6-OMe), 5.05 (d, 1H, J=11.0 Hz, H3), 5.17 (dd, 1H, J=11.0, 2.4 Hz, H13).

EXAMPLE 9

Synthesis of 11-{2-[N-methyl-N-(4-quinolylmethyl)amino]ethyl}amino-11-deoxy-3-O-(3-pyridyl)acetyl-5-O-desosaminyl-6-O-methylerythronolide A 11,12-cyclic carbamate (1) Following the same procedure as in Example 3(1) using 1.2 g (7.8 mmoles) of 4-quinolinecarboxaldehyde in place of nicotinealdehyde and 5.80 g (6.5 mmoles) of the compound obtained in Example 1(1), there was obtained 3.70 g (yield: 56%) of the 11-{2-[N-methyl-N-(4-quinolylmethyl)amino]ethyl}amino compound.

(2) Following the same procedure as in Example 3(2) using 3.60 g (3.5 mmoles) of the compound obtained in the above (1), there was obtained 2.40 g (yield: 80%) of the 3-hydroxyl compound.

(3) Following the same procedure as in Example 1(3) using 2.10 g (2.5 mmoles) of the compound obtained in the above (2), there was obtained 2.20 g (yield: 99%) of the 2'-O-acetyl compound.

(4) Following the same procedure as in Example 1(4) using 0.70 g (0.82 mmole) of the compound obtained in the above (3), there was obtained 0.36 g (yield: 47%) of the title compound.

Mass (FAB; 3-NBA) m/z: 932 [M+H]$^+$.

EXAMPLE 10

Synthesis of 11-{2-[N-methyl-N-4-quinolylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 2 using 0.70 g (0.82 mmole) of the compound obtained in Example 9(3), there was obtained 0.33 g (yield: 45%) of the title compound.

Mass (FAB; 3-NBA) m/z: 932 [M+H]$^+$.

EXAMPLE 11

Synthesis of 11-{3-[N-methyl-N-(3-pyridylmethyl)amino]propyl}amino-11-deoxy-3-O-(2-pyridyl)acetyl-5-O-desosaminyl-6-O-methylerythronolide A 11,12-cyclic carbamate (1) Carrying out the same reaction as in Example 1(1) using 14.6 g (16 mmoles) of 10,11-anhydro-2',4"-di-O-acetyl-12-O-imidazolylcarbonyl-6-O-methylerythromycin A and 4.0 ml (48 mmoles) of 1,3-diaminopropane, there was obtained 10.14 g (yield: 73%) of the 11-(3-aminopropyl)amino compound.

Mass (FAB) m/z: 872 [M+H]$^+$.

(2) Carrying out the same reactions as in Examples 3(1) and 3(2) using 5.8 g (6.7 mmoles) of the compound obtained in the above (1), there was obtained 2.81 g (yield: 54%) of the 3-hydroxyl compound.

Mass (FAB) m/z: 777 [M+H]$^+$.

(3) Carrying out the same reaction as in Example 1(3) using 2.30 g (3.0 mmoles) of the compound obtained in the above (2), there was obtained 2.22 g of the 2'-O-acetyl compound.

(4) Carrying out the same reaction as in Example 2 using 0.68 g (0.83 mmole) of the compound obtained in the above (3), there was obtained 0.58 g (yield: 78%) of the title compound.

Mass (FAB) m/z: 896 [M+H]$^+$.

EXAMPLE 12

Synthesis of 11-{3-[N-methyl-N-(3-pyridylmethyl)amino]propyl}amino-11-deoxy-3-O-(3-pyridyl)acetyl-5-O-desosaminyl-6-O-methylerythronolide A 11,12-cyclic carbamate Carrying out the same reaction as in Example 1(4) using 0.67 g (0.82 mmole) of the compound obtained in Example 11(3), there was obtained 0.46 g (yield: 63%) of the title compound.

Mass (FAB) m/z: 896 [M+H]$^+$.

EXAMPLE 13

Synthesis of 11-{3-[N,N-bis(3-pyridylmethyl)amino]propyl}amino-11-deoxy-3-O-(2-pyridyl)acetyl-5-O-desosaminyl-6-O-methylerythronolide A 11,12-cyclic carbamate (1) Carrying out the same N,N-bis(3-pyridylmethyl) amination as in Example 1(2) using 3.27 g (3.8 moles) of the compound obtained in Example 11(1), there was obtained 2.85 g (yield: 72%) of 4"-O-acetyl-11-{3-[N,N-bis(3-pyridylmethyl)amino]propyl}amino-11-deoxy-6-O-methylerythromycin A 11,12-cyclic carbamate.

Mass (FAB) m/z; 1054 [M+H]$^+$.

(2) A solution of 2.51 g (2.38 mmoles) of the compound obtained in the above (1) in 50 ml of 1N aqueous hydrochloric acid solution was stirred at room temperature overnight, made basic with 2N aqueous sodium hydroxide solution and then extracted with chloroform. The organic layer was dried over anhydrous magnesium sulfate, and the solvent was evaporated under reduced pressure to give 1.85 g of the residue, which was then purified by silica gel column chromatography (chloroform:methanol:aqueous ammonia=15:1:0.1) to give 1.18 g (yield: 58%) of the 3-hydroxyl compound.

Mass (FAB) m/z: 854 [M+H]$^+$.

(3) Carrying out the same reaction as in Example 1(3) using 1.04 g (1.22 mmoles) of the compound obtained in the above (2), there was obtained 1.15 g of the 2'-O-acetyl compound.

(4) Carrying out the same reaction as in Example 2 using 0.59 g (0.66 mmole) of the compound obtained in the above (3), there was obtained 0.42 g (yield: 66%) of the title compound.

Mass (FAB) m/z: 973 [M+H]$^+$.

EXAMPLE 14

Synthesis of 11-{3-[N,N-bis(3-pyridylmethyl)amino]propyl}amino-11-deoxy-3-O-(3-pyridyl)acetyl-5-O-desosaminyl-6-O-methylerythronolide A 11,12-cyclic carbamate Carrying out the same reaction as in Example 1(4) using 0.54 g (0.6 mmole) of the compound obtained in Example 13(3), there was obtained 0.25 g (yield: 42%) of the title compound.

Mass (FAB) m/z: 973 [M+H]$^+$.

EXAMPLE 15

Synthesis of 11-{3-[N-methyl-N-(2-pyridylmethyl)amino]propyl}amino-11-deoxy-3-O-(2-pyridyl)acetyl-5-O-desosaminyl-6-O-methylerythronolide A 11,12-cyclic carbamate (1) Carrying out the same reaction as in Example 3(1) using 4.91 g (5.6 mmoles) of the compound obtained in Example 11(1), there was obtained 2.08 g (yield: 38%) of the 11-{3-[N-methyl-N-(2-pyridylmethyl)amino]propyl}amino compound.

Mass (FAB) m/z: 977 [M+H]$^+$.

(2) 2.08 g (2.1 mmoles) of the compound obtained in the above (1) was treated in the same manner as in Example 13(2) for removal of the cladinose moiety, followed by the same reaction as in Example 1(3) to give 1.45 g of the 2'-O-acetyl compound.

(3) Carrying out the same reaction as in Example 2 using 0.51 g (0.63 mmole) of the compound obtained in the above (2), there was obtained 0.31 g (yield: 55%) of the title compound.

Mass (FAB) m/z: 896 [M+H]$^+$.

EXAMPLE 16

Synthesis of 11-{3-[N-methyl-N-(2-pyridylmethyl)amino]propyl}amino-11-deoxy-3-O-(3-pyridyl)acetyl-5-O-desosaminyl-6-O-methylerythronolide A 11,12-cyclic carbamate Carrying out the same reaction as in Example 1(4) using 0.51 g (0.63 mmole) of the compound obtained in Example 15(2), there was obtained 0.24 g (yield: 43%) of the title compound.

Mass (FAB) m/z: 896 [M+H]$^+$.

EXAMPLE 17

Synthesis of 11-{3-[N,N-bis(2-pyridylmethyl)amino]propyl}amino-11-deoxy-3-O-(2-pyridyl)acetyl-5-O-desosaminyl-6-O-methylerythronolide A 11,12-cyclic carbamate (1) Following the same procedures as in Examples 1(2) and 3(2) using 5.04 g(5.78 mmoles) of the compound obtained in Example 11(1) and 2.7 ml (28.4 mmoles) of 2-pyridinecarboxaldehyde, there was obtained 3.35 g (yield: 68%) of 11-{3-[N,N-bis(2-pyridylmethyl)-amino]propyl}amino-11-deoxy-5-O-desosaminyl-6-O-methylerythronolide A 11,12-cyclic carbamate.

(2) Carrying out the same reaction as in Example 1(3) using 3.1 g (3.63 mmoles) of the compound obtained in the above (1), there was obtained 3.18 g (yield: 98%) of the 2'-O-acetyl compound.

(3) Carrying out the same reaction as in Example 2 using 1.5 g (1.67 mmoles) of the compound obtained in the above (2), there was obtained 0.88 g (yield: 54%) of the title compound.

Mass (FAB) m/z: 973 [M+H]$^+$.

EXAMPLE 18

Synthesis of 11-{3-[N,N-bis(3-pyridylmethyl)amino]propyl}amino-11-deoxy-3-O-(2-pyridyl)acetyl-5-O-desosaminyl-6-O-methylerythronolide A 11,12-cyclic carbamate Carrying out the same reaction as in Example 1(4) using 1.5 g (1.67 mmoles) of the compound obtained in Example 17(2), there was obtained 1.47 g (yield: 90%) of the title compound.

Mass (FAB) m/z: 973 [M+H]$^+$.

EXAMPLE 19

Synthesis of 11-{5-[N-methyl-N-(3-pyridylmethyl)amino]pentyl}amino-11-deoxy-3-O-(3-pyridyl)acetyl-5-O-desosaminyl-6-O-methylerythronolide A 11,12-cyclic carbamate (1) Carrying out the same reaction as in Example 1(1) using 2.0 g (2.2 mmoles) of 10,11-anhydro-2',4"-di-O-acetyl-12-O-imidazolylcarbonyl-6-O-methylerythromycin A and 0.52 ml (4.4 mmoles) of 1,5-diaminopentane, there was obtained 1.20 g (yield: 61%) of the 4"-O-acetyl-11-(5-aminopentyl)amino-11-deoxy-6-O-methylerythromycin A 11,12-cyclic carbamate compound.

Mass (FAB) m/z: 900 [M+H]$^+$.

(2) Carrying out the same reactions as in Examples 3(1), 3(2), 1(3) and 1(4) using 1.0 g (1.11 mmoles) of the compound obtained in the above (1), there was obtained 0.36 g of the title compound.

Mass (FAB) m/z: 924 [M+H]$^+$.

EXAMPLE 20

Synthesis of 11-[2-(N-methyl-N-benzylamino)ethyl]amino-11-deoxy-3-O-(2-pyridyl)acetyl-5-O-desosaminyl-6-O-methylerythronolide A 11,12-cyclic carbamate (1) Carrying out the same reaction as in Example 3(1) using 2.4 g (2.8 mmoles) of the compound obtained in Example 1(1) and 0.29 ml (2.85 mmoles) of benzaldehyde, there was obtained 1.49 g (yield: 57%) of the 11-[2-(N-methyl-N-benzylamino)ethyl]amino compound.

Mass (FAB) m/z: 920 [M+H]$^+$ (2) Carrying out the same reactions as in Examples 3(2), 3(3) and 2, successively, using 0.5 g (0.54 mmole) of the compound obtained in the above (1), there was obtained 0.31 g (yield: 65%) of the title compound.

Mass (FAB) m/z: 881 [M+H]$^+$.

EXAMPLE 21

Synthesis of 11-{2-[N-methyl-N-(3-pyridylmethyl)amino]ethyl}amino-11-deoxy-3-O-(4-nitrophenyl)acetyl-5-O-desosaminyl-6-O-methylerythronolide A 11,12-cyclic carbamate Following the same procedure as in Example 2 using 0.60 g (0.75 mmole) of the compound obtained in Example 3(3) and p-nitrophenylacetic acid, there was obtained 0.31 g (yield: 45%) of the title compound.

Mass (IonSpray) m/z: 926.5 [M+H]$^+$; $^1$H-NMR (300 MHz, CDCl$_3$) δ(ppm): 0.71 (t, 3H, J=7.25 Hz, H15), 2.18 (s, 3H, NMe), 2.27 (s, 6H, NMe$_2$), 3.02(s, 3H, 6-OMe), 7.53 (m, 2H), 8.21 (m, 2H).

EXAMPLE 22

Synthesis of 11-{2-[N-methyl-N-(3-pyridylmethyl)amino]ethyl}amino-11-deoxy-3-O-nicotinoyl-5-O-desosaminyl-6-O-methylerythronolide A 11,12-cyclic carbamate Following the same procedure as in Example 2 using 0.60 g (0.75 mmole) of the compound obtained in Example 3(3) and nicotinic acid, there was obtained 0.50 g (yield; 75%) of the title compound.

Mass (IonSpray) m/z: 868.5 [M+H]$^+$; $^1$H-NMR (300 MHz, CDCl$_3$) δ(ppm): 0.76 (t, 3H, J=7.26 Hz, H15), 2.10 (s, 6H, NMe$_2$), 2.22 (s, 3H, NMe), 3.09(s, 3H, 6-OMe), 5.26 (dd, 1H, J=11.0, 2.0 Hz), 5.33 (d, 1H, J=11.2 Hz).

EXAMPLE 23

Synthesis of 11-{2-[N-methyl-N-(3-pyridylmethyl)amino]ethyl}amino-11-deoxy-3-O-picolinoyl-5-O-desosaminyl-6-O-methylerythronolide A 11,12-cyclic carbamate Following the same procedure as in Example 2 using 0.60 g (0.75 mmole) of the compound obtained in Example 3(3) and picolinic acid, there was obtained 0.21 g (yield: 32%) of the title compound.

Mass (IonSpray) m/z: 868.5 [M+H]$^+$; $^1$H-NMR (300 MHz, CDCl$_3$) δ(ppm): 0.75 (t, 3H, J=7.44 Hz, H15), 2.12 (s, 6H, NMe$_2$), 2.22 (s, 3H, NMe), 3.09 (s, 3H, 6-OMe), 5.26 (dd, 1H, J=11.2, 2.1 Hz), 5.36 (d, 1H, J=11.3 Hz).

EXAMPLE 24

Synthesis of 11-{2-[N-methyl-N-(3-pyridylmethyl)amino]ethyl}amino-11-deoxy-3-O-isonicotinoyl-5-O-desosaminyl-6-O-methylerythronolide A 11,12-cyclic carbamate Following the same procedure as in Example 2 using 0.60 g (0.75 mmole) of the compound obtained in Example 3(3) and isonicotinic acid, there was obtained 0.37 g (yield: 57%) of the title compound.

Mass (IonSpray) m/z: 868.5 [M+H]$^+$; $^1$H-NMR (300 MHz, CDCl$_3$) δ(ppm): 0.76 (t, 3H, J=7.26 Hz, H15), 2.10 (s, 6H, NMe$_2$), 2.22 (s, 3H, NMe), 3.08 (s, 3H, 6-OMe), 5.26 (dd, 1H, J=11.2, 2.1 Hz), 5.31 (d, 1H, J=11.2 Hz), 7.95 (m, 2H), 8.85 (m, 2H).

EXAMPLE 25

Synthesis of 11-{2-[N-methyl-N-(4-nitrobenzyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.61 g (4.0 mmoles) of 4-nitrobenzaldehyde in place of nicotinealdehyde and 2.80 g (3.4 mmoles) of the compound obtained in Example 1(1), there was obtained the 11-{2-[N-methyl-N-(4-nitrobenzyl)amino]ethyl}amino compound, followed by the same procedure as in Example 3(2) to give 0.90 g (yield: 32%) of the 3-hydroxyl compound.

(2) Following the same procedure as in Example 1(3) using 0.70 g (0.84 mmole) of the compound obtained in the above (1), there was obtained 0.75 g (yield: 99%) of the 2'-O-acetyl compound.

(3) Following the same procedure as in Example 2 using 0.50 g (0.57 mmole) of the compound obtained in the above (2), there was obtained 0.35 g (yield: 66%) of the title compound.

Mass (IonSpray) m/z: 926.6 [M+H]$^+$; $^1$H-NMR (300 MHz, CDCl$_3$) δ(ppm): 0.70 (t, 3H, J=7.26 Hz, H15), 2.20 (s, 3H, NMe), 2.30 (s, 6H, NMe$_2$), 3.02 (s, 3H, 6-OMe), 7.50 (m, 2H), 8.13 (m, 2H).

EXAMPLE 26

Synthesis of 11-{2-[N-methyl-N-(4-aminobenzyl)amino]ethyl}amino-11-deoxy-3-O-(2-pyridyl)acetyl-5-O-desosaminyl-6-O-methylerythronolide A 11,12-cyclic carbamate To a solution of 0.50 g (0.54 mmole) of the compound obtained in Example 22 in 5.0 ml of methanol were added 0.26 g (1.1 mmoles) of nickel chloride hexahydrate and 82 mg (2.2 mmoles) of sodium borohydride under ice-cooling, followed by stirring for 10 minutes. After the reaction, 25% aqueous ammonia was added to the reaction mixture, followed by extraction with chloroform. The organic layer was washed with a saturated aqueous sodium chloride solution and dried over anhydrous potassium carbonate, followed by evaporation of the solvent under reduced pressure. The residue was purified by silica gel column chromatography (chloroform:methanol:aqueous ammonia=20:1:0.1) to give 0.26 g (yield: 54%) of the title compound.

Mass (IonSpray) m/z: 896.6 [M+H]$^+$; $^1$H-NMR (500 MHz, CDCl$_3$) δ(ppm): 0.76 (t, 3H, J=7.3 Hz, H15), 2.18 (s, 3H, NMe), 2.29 (s, 6H, NMe$_2$), 2.97 (s, 3H, 6-OMe), 6.61 (m, 2H), 7.08 (m, 2H).

EXAMPLE 27

Synthesis of 11-{2-[N-methyl-N-(4-methoxybenzyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.44 ml (3.6 mmoles) of 4-methoxybenzaldehyde in place of nicotinealdehyde and 3.00 g (3.6 mmoles) of the compound obtained in Example 1(1), there was obtained the 11-{2-[N-methyl-N-(4-methoxybenzyl)amino]ethyl}amino compound, followed by the same procedure as in Example 3(2) to give 1.89 g (yield: 61%) of the 3-hydroxyl compound.

(2) Following the same procedure as in Example 1(3) using 1.80 g (2.1 mmoles) of the compound obtained in the above (1), there was obtained 1.80 g (yield: 95%) of the 2'-O-acetyl compound.

(3) Following the same procedure as in Example 2 using 0.80 g (0.88 mmole) of the compound obtained in the above (2), there was obtained 0.44 g (yield: 55%) of the title compound.

Mass (IonSpray) m/z: 911.6 [M+H]$^+$; $^1$H-NMR (500 MHz, CDCl$_3$) δ(ppm): 0.74 (t, 3H, J=7.5 Hz, H15), 2.17 (s, 3H, NMe), 2.29 (s, 6H, NMe$_2$), 3.02 (s, 3H, 6-OMe), 3.78 (s, 3H, Ph-OMe), 6.81 (m, 2H), 7.22 (m, 2H).

EXAMPLE 28

Synthesis of 11-[2-(N-methyl-N-furfurylamino)ethyl]amino-11-deoxy-3-O-(2-pyridyl)-acetyl-5-O-desosaminyl-6-O-methylerythronolide A 11,12-cyclic carbamate (1) Following the same procedure as in Example 3(1) using 0.30 ml (3.6 mmoles) of furfural in place of nicotinealdehyde and 3.00 g (3.6 mmoles) of the compound obtained in Example 1(1), there was obtained the 11-[2-(N-methyl-N-furfurylamino)ethyl]amino compound, followed by the same procedure as in Example 3(2) to give 1.20 g (yield: 40%) of the 3-hydroxyl compound.

(2) Following the same procedure as in Example 1(3) using 1.10 g (1.3 mmoles) of the compound obtained in the above (1), there was obtained 1.0 g (yield: 89%) of the 2'-O-acetyl compound.

(3) Following the same procedure as in Example 2 using 0.50 g (0.58 mmole) of the compound obtained in the above (2), there was obtained 0.26 g (yield: 52%) of the title compound.

Mass (IonSpray) m/z: 871.5 [M+H]$^+$; $^1$H-NMR (500 MHz, CDCl$_3$) δ(ppm): 0.80 (t, 3H, J=7.5 Hz, H15), 2.24 (s, 6H, NMe$_2$), 2.25 (s, 3H), 3.02 (s, 3H, NMe), 6.23 (m, 2H), 7.34 (m, 1H).

EXAMPLE 29

Synthesis of 11-{2-[N-methyl-N-(4-pyridylmethyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.34 ml (3.6 mmoles) of isonicotinealdehyde in place of nicotinealdehyde and 3.00 g (3.6 mmoles) of the compound obtained in Example 1(1), there was obtained the 11-{2-[N-methyl-N-(4-pyridylmethyl)amino]ethyl}amino compound, followed by the same procedure as in Example 3(2) to give 1.85 g (yield: 67%) of the 3-hydroxyl compound.

(2) Following the same procedure as in Example 1(3) using 1.60 g (2.1 mmoles) of the compound obtained in the above (1), there was obtained 1.56 g (yield: 92%) of the 2'-O-acetyl compound.

(3) Following the same procedure as in Example 2 using 0.50 g (0.62 mmole) of the compound obtained in the above (2), there was obtained 0.31 g (yield: 57%) of the title compound.

Mass (IonSpray) m/z: 882.6 [M+H]$^+$; $^1$H-NMR (500 MHz, CDCl$_3$) δ(ppm): 0.69 (t, 3H, J=7.5 Hz, H15), 2.20 (s, 3H, NMe), 2.30 (s, 6H, NMe$_2$), 3.02 (s, 3H, 6-OMe), 7.26 (m, 2H), 8.49 (m, 2H).

EXAMPLE 30

Synthesis of 11-{2-[N-methyl-N-(2-thienylmethyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.34 ml (3.6 mmoles) of thiophene-2-aldehyde in place of nicotinealdehyde and 3.00 g (3.6 mmoles) of the compound obtained in Example 1(1), there was obtained the 11-{2-[N-methyl-N-(2-thienylmethyl)amino]ethyl}amino compound, followed by the same procedure as in Example 3(2) to give 1.34 g (yield: 46%) of the 3-hydroxyl compound.

(2) Following the same procedure as in Example 1(3) using 1.20 g (1.5 mmoles) of the compound obtained in the above (1), there was obtained 1.24 g (yield: 99%) of the 2'-O-acetyl compound.

(3) Following the same procedure as in Example 2 using 0.50 g (0.62 mmole) of the compound obtained in the above (2), there was obtained 0.30 g (yield: 55%) of the title compound.

Mass (IonSpray) m/z: 887.5 [M+H]$^+$; $^1$H-NMR (500 MHz, CDCl$_3$) δ(ppm): 0.79 (t, 3H, J=7.5 Hz, H15), 2.29 (s, 3H, NMe), 2.30 (s, 6H, NMe$_2$), 3.03 (s, 3H, 6-OMe), 6.90 (m, 2H), 7.18 (m, 1H).

EXAMPLE 31

Synthesis of 11-{2-[N-methyl-N-(3,4,5-trimethoxybenzyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.71 g (3.6 mmoles) of 3,4,5-trimethoxybenzaldehyde in place of nicotinealdehyde and 3.00 g (3.6 mmoles) of the compound obtained in Example 1(1), there was obtained the 11-{2-[N-methyl-N-(3,4,5-trimethoxybenzyl)amino]ethyl}amino compound, followed by the same procedure as in Example 3(2) to give 1.99 g (yield: 60%) of the 3-hydroxyl compound.

(2) Following the same procedure as in Example 1(3) using 1.67 g (1.8 mmoles) of the compound obtained in the above (1), there was obtained 1.39 g (yield: 80%) of the 2'-O-acetyl compound.

(3) Following the same procedure as in Example 2 using 0.50 g (0.52 mmole) of the compound obtained in the above (2), there was obtained 0.33 g (yield: 65%) of the title compound.

Mass (IonSpray) m/z: 971.6 [M+H]$^+$; $^1$H-NMR (500 MHz, CDCl$_3$) δ(ppm): 0.68 (t, 3H, J=7.5 Hz, H15), 2.24 (s, 3H, NMe), 2.29 (s, 6H, NMe$_2$), 3.02 (s, 3H, 6-OMe), 3.82 (s, 3H, Ph-OMe), 3.86 (s, 6H, Ph-OMe), 6.61 (s, 2H).

EXAMPLE 32

Synthesis of 11-{2-[N-methyl-N-(4-tolylmethyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.39 ml (3.3 mmoles) of 4-tolualdehyde in place of nicotinealdehyde and 2.35 g (3.04 mmoles) of the compound obtained in Example 1(1), there was obtained the 11-{2-[N-methyl-N-(4-tolylmethyl)amino]ethyl}amino compound, followed by the same procedure as in Example 3(2) to give 2.28 g (yield: 97%) of the 3-hydroxyl compound.

(2) Following the same procedure as in Example 1(3) using 2.00 g (2.6 mmoles) of the compound obtained in the above (1), there was obtained 1.95 g (yield: 92%) of the 2'-O-acetyl compound.

(3) Following the same procedure as in Example 2 using 0.92 g (1.13 mmoles) of the compound obtained in the above (2), there was obtained 0.98 g (yield: 97%) of the title compound.

Mass (IonSpray) m/z: 895.6 [M+H]$^+$; $^1$H-NMR (300 MHz, CDCl$_3$) δ(ppm): 0.75 (t, 3H, J=7.26 Hz, H15), 2.18 (s, 3H, NMe), 2.29 (s, 6H, NMe$_2$), 2.31 (s, 3H, PhMe), 3.02 (s, 3H, 6-OMe), 3.44 (d, 1H, J=13.0 Hz), 3.70 (d, 1H, J=13.0 Hz), 7.08 (m, 2H), 7.19 (m, 2H).

EXAMPLE 33

Synthesis of 11-{2-[N-methyl-N-(2-tolylmethyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.39 ml (3.3 mmoles) of 2-tolualdehyde in place of nicotinealdehyde and 2.35 g (3.0 mmoles) of the compound obtained in Example 1(1), there was obtained the 11-{2-[N-methyl-N-(2-tolylmethyl)amino]ethyl}amino compound, followed by the same procedure as in Example 3(2) to give 2.24 g (yield: 96%) of the 3-hydroxyl compound.

(2) Following the same procedure as in Example 1(3) using 2.00 g (2.6 mmoles) of the compound obtained in the above (1), there was obtained 1.84 g (yield: 87%) of the 2'-O-acetyl compound.

(3) Following the same procedure as in Example 2 using 0.80 g (0.98 mmole) of the compound obtained in the above (2), there was obtained 0.48 g (yield: 50%) of the title compound.

Mass (IonSpray) m/z: 895.6 [M+H]$^+$; $^1$H-NMR (300 MHz, CDCl$_3$) δ(ppm): 0.72 (t, 3H, J=7.26 Hz, H15), 2.21 (s, 3H, NMe), 2.29 (s, 6H, NMe$_2$), 2.34 (s, 3H, PhMe), 3.00 (s, 3H, 6-OMe), 3.51 (d, 1H, J=13.3 Hz), 3.62 (d, 1H, J=13.3 Hz), 7.10 (m, 3H), 7.32 (m, 1H).

EXAMPLE 34

Synthesis of 11-{2-[N-methyl-N-(3-tolylmethyl)amino]ethyl}amino-11-deoxy-3-O-(2-pyridyl)acetyl-5-O-desosaminyl-6-O-methylerythronolide A 10 11,12-cyclic carbamate (1) Following the same procedure as in Example 3(1) using 0.39 ml (3.3 mmoles) of 3-tolualdehyde in place of nicotinealdehyde and 2.35 g (3.0 mmoles) of the compound obtained in Example 1(1), there was obtained the 11-{2-[N-methyl-N-(3-tolylmethyl)amino]ethyl}amino compound, followed by the same procedure as in Example 3(2) to give 1.73 g (yield: 74%) of the 3-hydroxyl compound.

(2) Following the same procedure as in Example 1(3) using 0.86 g (1.1 mmoles) of the compound obtained in the above (1), there was obtained 0.85 g (yield: 95%) of the 2'-O-acetyl compound.

(3) Following the same procedure as in Example 2 using 0.75 g (0.92 mmole) of the compound obtained in the above (2), there was obtained 0.45 g (yield: 55%) of the title compound.

Mass (IonSpray) m/z: 895.6 [M+H]$^+$; $^1$H-NMR (300 MHz, CDCl$_3$) δ(ppm): 0.75 (t, 3H, J=7.26 Hz, H15), 2.19 (s, 3H, NMe), 2.30 (s, 6H, NMe$_2$), 2.32 (s, 3H, PhMe), 3.02 (s, 3H, 6-OMe), 3.44 (d, 1H, J=13.1 Hz), 3.70 (d, 1H, J=13.1 Hz), 7.01 (m, 1H), 7.13 (m, 3H).

EXAMPLE 35

Synthesis of 11-{2-[N-methyl-N-(cyclohexylmethyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.34 ml (3.3 mmoles) of cyclohexanecarboxaldehyde in place of nicotinealdehyde and 2.35 g (3.04 mmoles) of the compound obtained in Example 1(1), there was obtained the 11-{2-[N-methyl-N-(cyclohexylmethyl)amino]ethyl}amino compound, followed by the same procedure as in Example 3(2) to give 0.87 g (yield: 37%) of the 3-hydroxyl compound.

(2) Following the same procedure as in Example 1(3) using 0.78 g (1.02 mmoles) of the compound obtained in the above (1), there was obtained 0.76 g (yield: 92%) of the 2'-O-acetyl compound.

(3) Following the same procedure as in Example 2 using 0.70 g (0.87 mmole) of the compound obtained in the above (2), there was obtained 0.57 g (yield: 74%) of the title compound.

Mass (IonSpray) m/z: 887.6 [M+H]$^+$; $^1$H-NMR (300 MHz, CDCl$_3$) δ(ppm): 0.81 (t, 3H, J=7.26 Hz, H15), 2.24 (s, 3H, NMe), 2.29 (s, 6H, NMe$_2$), 3.03 (s, 3H, 6-OMe), 5.07 (d, 1H, J=11.2 Hz, H3), 5.13 (dd, 1H, J=11.2, 2.48 Hz, H13).

EXAMPLE 36

Synthesis of 11-{2-[N-methyl-N-(1-methyl-2-pyrrolylmethyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.36 g (3.3 mmoles) of 1-methylpyrrole-2-carboxaldehyde in place of nicotinealdehyde and 2.35 g (3.04 mmoles) of the compound obtained in Example 1(1), there was obtained the 11-{2-[N-methyl-N-(N-methyl-2-pyrrolylmethyl)amino]ethyl}amino compound, followed by the same procedure as in Example 3(2) to give 0.57 g (yield: 25%) of the 3-hydroxyl compound.

(2) Following the same procedure as in Example 1(3) using 0.40 g (0.52 mmole) of the compound obtained in the above (1), there was obtained 0.41 g (yield: 98%) of the 2'-O-acetyl compound.

(3) Following the same procedure as in Example 2 using 0.40 g (0.50 mmole) of the compound obtained in the above (2), there was obtained 0.40 g (yield: 90%) of the title compound.

Mass (IonSpray) m/z: 884.6 [M+H]$^+$; $^1$H-NMR (300 MHz, CDCl$_3$) δ(ppm): 0.81 (t, 3H, J=7.26 Hz, H15), 2.16 (s, 3H, NMe), 2.29 (s, 6H, NMe$_2$), 3.03 (s, 3H, 6-OMe), 5.99 (m, 2H), 6.50 (m, 1H).

EXAMPLE 37

Synthesis of 11-{2-[N-methyl-N-(2-methoxybenzyl)amino]ethyl}amino-11-deoxy-3-O-(2-pyridyl)acetyl-5-O-desosaminyl-6-O-methylerythronolide A 11,12-cyclic carbamate (1) Following the same procedure as in Example 3(1) using 0.40 ml (3.6 mmoles) of 2-methoxybenzaldehyde in place of nicotinealdehyde and 2.35 g (3.04 mmoles) of the compound obtained in Example 1(1), there was obtained the 11-{2-[N-methyl-N-(2-methoxylbenzyl)amino]ethyl}amino compound, followed by the same procedure as in Example 3(2) to give 2.23 g (yield: 85%) of the 3-hydroxyl compound.

(2) Following the same procedure as in Example 1(3) using 2.00 g (2.3 mmoles) of the compound obtained in the above (1), there was obtained 2.05 g (yield: 98%) of the 2'-O-acetyl compound.

(3) Following the same procedure as in Example 2 using 1.16 g (1.3 mmoles) of the compound obtained in the above (2), there was obtained 0.61 g (yield: 52%) of the title compound.

Mass (IonSpray) m/z: 911.6 [M+H]$^+$; $^1$H-NMR (300 MHz, CDCl$_3$) δ(ppm): 0.73 (t, 3H, J=7.26 Hz, H15), 2.25 (s, 3H, NMe), 2.29 (s, 6H, NMe$_2$), 3.00 (s, 3H, 6-OMe), 3.62 (d, 1H, J=11.3 Hz), 3.69 (d, 1H, J=11.3 Hz), 3.80 (s, 3H, Ph-OMe), 6.82 (m, 1H), 6.90 (m, 1H), 7.16 (m, 1H), 7.42 (m, 1H).

EXAMPLE 38

Synthesis of 11-{2-[N-methyl-N-(4-fluorobenzyl)amino]ethyl}amino-11-deoxy-3-O-(2-pyridyl)acetyl-5-O-desosaminyl-6-O-methylerythronolide A 11,12-cyclic carbamate (1) A solution of 100 g (120 mmoles) of the compound obtained in Example 1(1) in 150 ml of 1N aqueous hydrochloric acid solution was stirred at 70° C. for an hour. The mixture was cooled to room temperature and extracted with chloroform. The aqueous layer was made basic with 2N aqueous sodium hydroxide solution and extracted with chloroform. The organic layer was washed with a saturated aqueous sodium chloride solution and dried over anhydrous magnesium sulfate, followed by evaporation of the solvent. The residue was crystallized from ether to give 49 g (yield: 63%) of the 3-hydroxyl compound.

(2) To a solution of 44.5 g (67.7 mmoles) of the compound obtained in the above (1) in 400 ml of methylene chloride were added 100 ml of water, 28.0 g (339 mmoles) of sodium bicarbonate and 24.0 ml (169 mmoles) of benzylchloroformate, followed by reaction at room temperature for an hour. The reaction mixture was extracted with chloroform, and the organic layer was washed with a saturated aqueous sodium chloride solution, and dried over anhydrous magnesium sulfate, followed by evaporation of the solvent under reduced pressure to give the N,O-bis(benzyloxycarbonyl) compound. To a solution of the compound in 500 ml of methylene chloride were successively added 23.4 g (135 mmoles) of 2-pyridylacetic acid hydrochloride, 25.9 g (135 mmoles) of 1-(3-dimethylaminopropyl)-3-ethylcarbodiimide hydrochloride and 0.82 g (6.7 mmoles) of 4-dimethylaminopyridine under ice-cooling, followed by stirring at room temperature for 2 hours. The reaction solution was washed with water and a saturated aqueous sodium chloride solution, and the organic layer was dried over anhydrous magnesium sulfate, followed by evaporation of the solvent under reduced pressure. The residue was purified by silica gel column chromatography (acetone:hexane:triethylamine=6:10:0.3) to give 50.0 g (yield: 71%) of the 3-O-(2-pyridyl)acetyl compound.

(3) To a solution of 50.0 g of the compound obtained in the above (2) in methanol was added 10 g of 5% palladium-carbon, followed by stirring under a hydrogen stream for 4 hours. After the reaction, the palladium-carbon was removed by filtration, and the filtrate was concentrated to give the crude product, which was then recrystallized from isopropyl ether to give 35.5 g (yield: 95%) of 11-(2-aminoethyl)amino-11-deoxy-3-O-(2-pyridyl)acetyl-5-O-desosaminyl-6-O-methylerythronolide A 11,12-cyclic carbamate.

Mass (IonSpray) m/z: 777.5 [M+H]$^+$; $^1$H-NMR (300 MHz, CDCl$_3$) δ(ppm): 0.82 (t, 3H, J=7.26 Hz, H15), 2.29 (s, 3H, NMe$_2$), 3.03 (s, 3H, 6-OMe), 5.06 (1H, d, J=11.2 Hz, H3), 7.22 (m, 2H), 7.37 (m, 1H), 7.69 (m, 1H), 8.57 (m, 1H).

(4) To a solution of 1.00 g (1.29 mmoles) of the compound obtained in the above (3) in 10 ml of methanol were added 0.15 ml (1.42 mmoles) of 4-fluorobenzaldehyde and 0.3 ml (5.0 mmoles) of acetic acid, then 0.55 g (2.58 mmoles) of sodium triacetoxyborohydride under ice-cooling. The temperature was turned to room temperature, followed by stirring for an hour. Then, 0.20 ml of 37% aqueous formaldehyde solution and 0.55 g (2.58 mmoles) of sodium triacetoxyborohydride were added to the mixture, and the temperature was turn to room temperature, followed by stirring for 4 hours. The mixture was made basic with 4N sodium hydroxide and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 0.38 g (yield: 33%) of the title compound.

Mass (IonSpray) m/z: 899.5 [M+H]$^+$; $^1$H-NMR (300 MHz, CDCl$_3$) δ(ppm): 0.72 (t, 3H, J=7.26 Hz, H15), 2.17 (s, 3H, NMe), 2.29 (s, 6H, NMe$_2$), 3.03 (s, 3H, 6-OMe), 6.94 (m, 2H), 7.27 (m, 2H).

EXAMPLE 39
Synthesis of 11-{2-[N-ethyl-N-(3-pyridylmethyl)amino]ethyl}amino-11-deoxy-3-O-(2-pyridyl)acetyl-5-O-desosaminyl-6-O-methylerythronolide A 11,12-cyclic carbamate Carrying out the same reaction as in Example 3(1) using 0.66 g(0.85 mmole) of the compound obtained in Example 38(3) and 0.16 ml(2.58 mmoles) of 90% acetaldehyde in place of 37% aqueous formaldehyde solution, there was obtained 0.64 g of the title compound.

MS (SIMS); m/z 896 [M+H]$^+$; $^1$H-NMR (500 MHz, CDCl$_3$) δ(ppm): 2.29 (6H, s, N(CH$_3$)$_2$), 2.98 (3H, s, 6-OCH$_3$), 5.05 (1H, d, J=11.0 Hz, $\overline{3\text{-H}}$), 5.09 (1H, dd, J=11.0, 2.4 Hz, 13-H). $^{13}$C-NMR (125 MHz, CDCl$_3$) δ(ppm): 40.3 (Q, N(CH$_3$)$_2$), 50.1 (Q, 6-OCH$_3$), 174.3 (S, C1), 215.7 (S, C9).

EXAMPLE 40
Synthesis of 11-{2-[N-methyl-N-(2-hydroxybenzyl)amino]ethyl}amino-11-deoxy-$^3$-O-(2-pyridyl)acetyl-5-O-desosaminyl-6-O-methylerythronolide A 11,12-cyclic carbamate Following the same procedure as in Example 38(4) using 0.21 ml (1.94 mmoles) of 2-hydroxybenzaldehyde in place of 4-fluorobenzaldehyde, there was obtained 1.05 g (yield: 67%) of the title compound.

Mass (IonSpray) m/z: 897.5 [M+H]$^+$; $^1$H-NMR (300 MHz, CDCl$_3$) δ(ppm): 0.79 (t, 3H, J=7.08 Hz, H15), 2.29 (s, 6H, NMe$_2$), 2.33 (s, 3H, NMe), 3.01 (s, 3H, 6-OMe), 6.78 (m, 2H), 6.95 (m, 1H), 7.13 (m, 1H).

EXAMPLE 41
Synthesis of 11-{2-[N-methyl-N-(2-fluorobenzyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.15 ml (1.42 mmoles) of 2-fluorobenzaldeyde in place of 4-fluorobenzaldehyde, there was obtained 0.50 g (yield: 43%) of the title compound.

Mass (IonSpray) m/z: 899.5 [M+H]$^+$; $^1$H-NMR (300 MHz, CDCl$_3$) δ(ppm): 0.73 (t, 3H, J=7.26 Hz, H15), 2.24 (s, 3H, NMe), 2.29 (s, 6H, NMe$_2$), 3.03 (s, 3H, 6-OMe), 3.62 (d, 1H, J=13.6 Hz), 3.79 (d, 1H, J=13.6 Hz), 6.97 (m, 1H), 7.06 (m, 1H), 7.16 (m, 1H), 7.42 (m, 1H).

EXAMPLE 42
Synthesis of 11-{2-[N-methyl-N-(2-nitrobenzyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.22 g (1.42 mmoles) of 2-nitrobenzaldehyde in place of 4-fluorobenzaldehyde, there was obtained 0.25 g (yield: 21%) of the title compound.

Mass (IonSpray) m/z: 926 [M+H]$^+$; $^1$H-NMR (300 MHz, CDCl$_3$) δ(ppm): 0.67 (t, 3H, J=7.26 Hz, H15), 2.24 (s, 3H, NMe), 2.30 (s, 6H, NMe$_2$), 3.00 (s, 3H, 6-OMe), 7.34 (m, 1H), 7.54 (m, 1H), 7.84 (m, 1H).

EXAMPLE 43
Synthesis of 11-{2-[N-methyl-N-(2-aminobenzyl)amino]ethyl}amino-11-deoxy-3-O-(2-pyridyl)acetyl-5-O-desosaminyl-6-O-methylerythronolide A 11,12-cyclic carbamate Following the same procedure as in Example 26 using 0.21 g (0.23 mmole) of the compound obtained in Example 42, there was obtained 0.15 g (yield: 73%) of the title compound.

Mass (IonSpray) m/z; 896 [M+H]$^+$; $^1$H-NMR (300 MHz, CDCl$_3$) δ(ppm): 0.80 (t, 3H, J=7.26 Hz, H15), 2.17 (s, 3H, NMe), 2.29 (s, 6H, NMe$_2$), 3.03 (s, 3H, 6-OMe), 3.59 (m, 2H), 4.72 (brs, 2H), 6.60 (m, 2H), 6.96 (m, 1H), 7.04 (m, 1H).

EXAMPLE 44
Synthesis of 11-{2-[N-methyl-N-(2-cyanobenzyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.20 g (1.54 mmoles) of 2-cyanobenzaldehyde in place of 4-fluorobenzaldehyde, there was obtained 0.25 g (yield: 22%) of the title compound.

Mass (IonSpray) m/z: 906 [M+H]$^+$; $^1$H-NMR (300 MHz, CDCl$_3$) δ(ppm): 0.70 (t, 3H, J=7.26 Hz, H15), 2.26 (s, 3H, NMe), 2.30 (s, 6H, NMe$_2$), 3.00 (s, 3H, 6-OMe), 7.29 (m, 1H), 7.52 (m, 1H), 7.58 (m, 1H), 7.66 (m, 1H).

EXAMPLE 45
Synthesis of 11-{2-[N-methyl-N-(2-hydroxy-4-methoxybenzyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.32 g (2.14 mmoles) of 2-hydroxy-4-methoxybenzaldehyde in place of 4-fluorobenzaldehyde, there was obtained 0.73 g (yield: 44%) of the title compound.

Mass (IonSpray) m/z: 927 [M+H]$^+$; $^1$H-NMR (300 MHz, CDCl$_3$) δ(ppm): 0.80 (t, 3H, J=7.26 Hz, H15), 2.29 (s, 6H, NMe$_2$), 2.32 (s, 3H, NMe), 3.01 (s, 3H, 6-OMe), 3.75 (s, 3H, Ph-OMe), 6.31 (dd, 1H, J=8.32, 2.48 Hz), 6.39 (d, 1H, J=2.48 Hz), 6.83 (d, 1H, J=8.32 Hz).

EXAMPLE 46
Synthesis of 11-{2-[N-methyl-N-(2-benzofuranylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.49 g (3.35 mmoles) of benzofuran-2-carboxaldehyde in place of 4-fluorobenzaldehyde, there was obtained 0.77 g (yield: 33%) of the title compound.

Mass (IonSpray) m/z: 921 [M+H]$^+$; $^1$H-NMR (300 MHz, CDCl$_3$) δ(ppm): 0.77 (t, 3H, J=7.26 Hz, H15), 2.30 (s, 6H, NMe$_2$), 2.39 (s, 3H, NMe), 3.00 (s, 3H, 6-OMe), 6.48 (m, 1H), 7.14~7.24 (m, 3H), 7.42 (m, 1H), 7.50 (m, 1H).

EXAMPLE 47
Synthesis of 11-{2-[N-methyl-N-(4-acetamidobenzyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.55 g (3.35 mmoles) of 4-acetamidobenzaldehyde in place of 4-fluorobenzaldehyde, there was obtained 0.96 g (yield: 40%) of the title compound.

Mass (IonSpray) m/z: 938 [M+H]$^+$; $^1$H-NMR (300 MHz, CDCl$_3$) δ(ppm): 0.76 (t, 3H, J=7.26 Hz, H15), 2.03 (s, 3H, NAc), 2.24 (s, 3H, NMe), 2.29 (s, 6H, NMe$_2$), 2.74 (s, 3H, 6-OMe), 7.24 (m, 3H), 7.32 (m, 3H), 7.64 (brs, 1H, NHAc).

EXAMPLE 48
Synthesis of 11-{2-[N-methyl-N-(2,3-methylenedioxybenzyl)amino]ethyl}amino-11-deoxy-3-O-

(2-pyridyl)acetyl-5-O-desosaminyl-6-O-methylerythronolide A 11,12-cyclic carbamate Following the same procedure as in Example 38(4) using 0.16 ml (1.42 mmoles) of 2,3-methylenedioxybenzaldehyde in place of 4-fluorobenzaldehyde, there was obtained 0.63 g (yield: 54%) of the title compound.

Mass (IonSpray) m/z: 911.5 [M+H]$^+$; $^1$H-NMR (300 MHz, CDCl$_3$) δ(ppm): 0.74 (t, 3H, J=7.26 Hz, H15), 2.29 (s, 6H, NMe$_2$), 3.01 (s, 3H, 6-OMe), 5.92 (m, 2H), 6.69 (dd, 1H, J=7.61, 1.96 Hz), 6.73 (t, 1H, J=7.61 Hz), 6.80 (dd, 1H, J=7.61, 1.96 Hz).

EXAMPLE 49

Synthesis of 11-{2-[N-methyl-N-(4-dimethylaminobenzyl)amino]ethyl}amino-11-deoxy-3-O-(2-pyridyl)acetyl-5-O-desosaminyl-6-O-methylerythronolide A 11,12-cyclic carbamate Following the same procedure as in Example 38(4) using 0.13 g (1.02 mmoles) of 4-dimethylaminoenzaldehyde in place of 4-fluorobenzaldehyde, there was obtained 0.56 g (yield: 67%) of the title compound.

Mass (IonSpray) m/z: 924.5 [M+H]$^+$.

EXAMPLE 50

Synthesis of 11-{2-[N-(2-hydroxy-4-methoxybenzyl)amino]ethyl}amino-11-deoxy-3-O-(2-pyridyl)acetyl-5-O-desosaminyl-6-O-methylerythronolide A 11,12-cyclic carbamate To a solution of 1.38 g (1.78 mmoles) of the compound obtained in Example 38(3) in 20 ml of methanol were added 0.32 9 (2.14 mmoles) of 2-hydroxy-4-methoxybenzaldehyde and 0.40 ml (6.67 mmoles) of acetic acid, then 0.75 g (3.55 mmoles) of sodium triacetoxyborohydride under ice-cooling. The temperature was turned to room temperature, followed by stirring for 4 hours. The mixture was made basic with 4N sodium hydroxide and extracted with diethyl ether. The organic layer was dried over anhydrous potassium carbonate, followed by evaporation of the solvent under reduced pressure. The residue was purified by silica gel column chromatography (chloroform:methanol:aqueous ammonia=20:1:0.1) to give 0.98 g (yield: 60%) of the title compound.

Mass (IonSpray) m/z: 913 [M+H]$^+$; $^1$H-NMR (300 MHz, CDCl$_3$) δ(ppm): 0.82 (t, 3H, J=7.26 Hz, H15), 2.29 (s, 6H, NMe$_2$), 3.02 (s, 3H, 6-OMe), 3.75 (s, 3H, Ph-OMe), 6.31 (dd, 1H, J=8.32, 2.48 Hz), 6.40 (d, 1H, J=2.48 Hz), 6.87 (d, 1H, J=8.32 Hz).

EXAMPLE 51

Synthesis of 11-{2-[N-(4-quinolylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 50 using 0.24 g (1.55 mmoles) of 4-quinolinecarboxaldehyde in place of 2-hydroxy-4-methoxybenzaldehyde, there was obtained 0.42 g (yield: 36%) of the title compound.

Mass (IonSpray) m/z: 918.5 [M+H]$^+$;

EXAMPLE 52

Synthesis of 11-{2-[N-(3H-1-oxaisoindolyl)amino]ethyl}amino-11-deoxy-3-O-(2-pyridyl)acetyl-5-O-desosaminyl-6-O-methylerythronolide A 11,12-cyclic carbamate Following the same procedure as in Example 50 using 0.55 g (3.35 imoles) of 2-methoxycarbonylbenzaldehyde in place of 2-hydroxy-4-methoxybenzaldehyde, there was obtained 1.01 g (yield: 44%) of the title compound.

Mass (IonSpray) m/z: 893 [M+H]$^+$; $^1$H-NMR (300 MHz, CDCl$_3$) δ(ppm): 0.83 (t, 3H, J=7.26 Hz, H15), 2.29 (s, 6H, NMe$_2$), 3.12 (s, 3H, 6-OMe), 4.45 (d, 1H, J=16.6 Hz), 4.60 (d, 1H, J=16.6 Hz), 7.41 (m, 2H), 7.50 (m, 1H), 7.82 (m, 1H).

EXAMPLE 53

Synthesis of 11-[2-(N-nicotinoyl)aminoethyl]amino-11-deoxy-3-O-(2-pyridyl)-acetyl-5-O-desosaminyl-6-O-methylerythronolide A 11,12 cyclic carbamate To a solution of 0.50 g (0.64 mmole) of the compound obtained in Example 38(3) in 10 ml of methylene chloride were added 0.14 g (0.77 mmole) of nicotinoyl chloride hydrochloride and 0.12 ml (1.54 mmoles) of pyridine, followed by stirring at room temperature for an hour. The reaction solution was made basic with 4N sodium hydroxide and extracted with chloroform. The organic layer was dried over anhydrous potassium carbonate, followed by evaporation of the solvent under reduced pressure. The residue was purified by silica gel column chromatography (chloroform:methanol:aqueous ammonia=20:1:0.1) to give 0.33 g (yield: 59%) of the title compound.

Mass (IonSpray) m/z: 882.5 [M+H]$^+$; $^1$H-NMR (300 MHz, CDCl$_3$) δ(ppm): 0.65 (t, 3H, J=7.26 Hz, H15), 2.29 (s, 6H, NMe$_2$), 3.08 (s, 3H, 6-OMe), 7.32 (dd, 1H, J=7.96, 4.96 Hz), 7.80 (brt, 1H, J=4.78 Hz), 8.16 (ddd, 1H, J=7.96, 1.59, 1.59 Hz), 8.67 (dd, 1H, J=4.96, 1.59 Hz), 9.03 (d, 1H, J=1.59 Hz).

EXAMPLE 54

Synthesis of 11-[2-(N-benzoyl)aminoethyl]amino-11-deoxy-3-O-(2-pyridyl)acetyl-5-O-desosaminyl-6-O-methylerythronolide A 11,12-cyclic carbamate Following the same procedure as in Example 53 using benzoyl chloride in place of nicotinoyl chloride hydrochloride, there was obtained 0.35 g (yield: 62%) of the title compound.

Mass (IonSpray) m/z: 881.5 [M+H]$^+$; $^1$H-NMR (300 MHz, CDCl$_3$) δ(ppm): 0.61 (t, 3H, J=7.26 Hz, H15), 2.29 (s, 6H, NMe$_2$), 3.09 (s, 3H, 6-OMe), 7.32–7.46 (m, 4H), 7.84 (m, 2H).

EXAMPLE 55

Synthesis of 11-{2-[N-(1-naphthoyl)amino]ethyl}amino-11-deoxy-3-O-(2-pyridyl)-acetyl-5-O-desosaminyl-6-O-methylerythronolide A 11,12-cyclic carbamate Following the same procedure as in Example 53 using 1-naphthoyl chloride in place of nicotinoyl chloride hydrochloride, there was obtained 0.40 g (yield: 67%) of the title compound.

Mass (IonSpray) m/z: 931.6 [M+H]$^+$.

EXAMPLE 56

Synthesis of 11-{2-[N-(4-biphenylcarbonyl)amino]ethyl}amino-11-deoxy-3-O-(2-pyridyl)acetyl-5-O-desosaminyl-6-O-methylerythronolide A 11,12-cyclic carbamate Following the same procedure as in Example 53 using 4-biphenylcarbonyl chloride in place of nicotinoyl chloride hydrochloride, there was obtained 0.38 g (yield: 62%) of the title compound.

Mass (IonSpray) m/z: 957.6 [M+H]$^+$.

EXAMPLE 57

Synthesis of 11-{2-[N-(3-quinolinoyl)amino]ethyl}amino-11-deoxy-3-O-(2-pyridyl)-acetyl-5-O-desosaminyl-6-O-methylerythronolide A 11,12-cyclic carbamate To a solution of 0.50 g (0.64 mmole) of the compound obtained in Example 38(3) in 10 ml of methylene chloride were added 0.13 g (0.77 mmole) of 3-quinolylcarboxylic acid, 0.15 g (0.77 nmole) of 1-(3-dimethylaminopropyl)-3-ethylcarbodiimide hydrochloride and 0.05 g (0.41 mmole) of 4-dimethylaminopyridine, followed by stirring at room temperature for an hour. The reaction solution was washed with water and a saturated aqueous sodium chloride solution, and the organic layer was dried over anhydrous magnesium sulfate, followed by evaporation of the solvent under reduced pressure. The residue was purified by silica gel column chromatography (chloroform:methanol:aqueous ammonia=20:1:0.1) to give 0.26 g (yield: 44%) of the title compound.

Mass (IonSpray) m/z: 932.6 [M+H]$^+$; $^1$H-NMR (300 MHz, CDCl$_3$) δ(ppm): 0.57 (t, 3H, J=7.26 Hz, H15), 2.29 (s, 6H, NMe$_2$), 3.11 (s, 3H, 6-OMe), 7.56 (m, 1H), 7.77 (m, 1H), 7.84 (brd, 1H, J=7.8 Hz), 7.92 (brt, 1H, J=5.0 Hz), 8.15 (d, 1H, J=8.3 Hz), 8.62 (d, 1H, J=2.0 Hz), 9.36 (d, 1H, J=2.3 Hz).

EXAMPLE 58
Synthesis of 11-{2-[N-(2-nitrobenzylidene)amino]ethyl}amino-11-deoxy-3-O-(2-pyridyl)acetyl-5-O-desosaminyl-6-O-methylerythronolide A 11,12-cyclic carbamate To a solution of 2.00 g (2.58 mmoles) of the compound obtained in Example 38(3) in 30 ml of methanol were added 0.44 g (2.84 mmoles) of 2-nitrobenzaldehyde and 0.6 ml (10.0 mmoles) of acetic acid, followed by stirring for an hour. The reaction solution was made basic with 4N sodium hydroxide and extracted with chloroform. The organic layer was dried over anhydrous magnesium sulfate, followed by evaporation of the solvent under reduced pressure. The residue was purified by silica gel column chromatography (chloroform:methanol:aqueous ammonia=20:1:0.1) to give 1.32 g (yield: 56%3 of the title compound.

Mass (IonSpray) m/z: 910.5 [M+H]$^+$; $^1$H-NMR (300 MHz, CDCl$_3$) δ(ppm): 0.50 (t, 3H, J=7.26 Hz, H15), 2.30 (s, 6H, NMe$_2$), 3.08 (s, 3H, 6-OMe), 8.83 (s, 1H, —N═CH).

EXAMPLE 59
Synthesis of 11-{2-[N-(2-cyanobenzylidene)amino]ethyl}amino-11-deoxy-3-O-(2-pyridyl)acetyl-5-O-desosaminyl-6-O-methylerythronolide A 11,12-cyclic carbamate Following the same procedure as in Example 58 using 0.20 g (1.54 mmoles) of 2-cyanobenzaldehyde in place of 2-nitrobenzaldehyde, there was obtained 0.53 g (yield: 47%) of the title compound.

Mass (IonSpray) m/z: 890 [M+H]$^+$; $^1$H-NMR (300 MHz, CDCl$_3$) δ(ppm): 0.61 (t, 3H, J=7.25 Hz, H15), 2.29 (s, 6H, NMe$_2$), 3.08 (s, 3H, 6-OMe), 8.80 (s, 1H, —N═CH).

EXAMPLE 60
Synthesis of 11-{2-[N-(2-imidazolylmethylene)amino]ethyl}amino-11-deoxy-3-O-(2-pyridyl)acetyl-5-O-desosaminyl-6-O-methylerythronolide A 11,12-cyclic carbamate Following the same procedure as in Example 58 using 0.32 g (3.35 mmoles) of imidazole-2-carboxaldehyde in place of 2-nitrobenzaldehyde, there was obtained 0.60 g (yield: 27%) of the title compound.

Mass (IonSpray) m/z: 855 [M+H]$^+$; $^1$H-NMR (300 MHz, CDCl$_3$) δ(ppm): 0.66 (t, 3H, J=7.43 Hz, H15), 2.29 (s, 6H, NMe$_2$), 2.89 (s, 3H, 6-OMe), 8.24 (s, 1H, —N═CH).

EXAMPLE 61
Synthesis of 11-{2-[N-(2-trifluoromethylbenzylidene)amino]ethyl}amino-11-deoxy-3-O-(2-pyridyl)acetyl-5-O-desosaminyl-6-O-methylerythronolide A 11,12-cyclic carbamate Following the same procedure as in Example 58 using 0.20 ml (1.55 mmoles) of 2-trifluoromethylbenzaldehyde in place of 2-nitrobenzaldehyde, there was obtained 0.78 g (yield: 65%) of the title compound.

Mass (IonSpray) m/z: 933.5 [M+H]$^+$; $^1$H-NMR (300 MHz, CDCl$_3$) δ(ppm): 0.55 (t, 3H, J=7.26 Hz, H15), 2.29 (s, 6H, NMe$_2$), 3.08 (s, 3H, 6-OMe), 8.78 (s, 1H, —N═CH).

EXAMPLE 62
Synthesis of 11-{2-[N-acetyl-N-(3-pyridylmethyl)amino]ethyl}amino-11-deoxy-3-O-(2-pyridyl)acetyl-5-O-desosaminyl-6-O-methylerythronolide A 11,12-cyclic carbamate (1) To a solution of 10.3 g (12.0 mmoles) of the compound obtained in Example 1(1) in 100 ml of methanol were added 1.1 ml (12.0 mmoles) of nicotinealdehyde and 2.0 ml (35.0 mmoles) of acetic acid, then 0.9 g (14.3 mmoles) of sodium cyanoborohydride under ice-cooling. The mixture was stirred at room temperature for 3 hours. After the reaction, the mixture was diluted with ethyl acetate, and successively washed with an aqueous sodium hydroxide solution and a saturated aqueous sodium chloride solution. The organic layer was dried over anhydrous magnesium sulfate, followed by evaporation of the solvent under reduced pressure to give 10.5 g of 4"-O-acetyl-11-{2-[N-(3-pyridylmethyl)amino]ethyl}amino-11-deoxy-6-O-methylerythromycin A 11,12-cyclic carbamate.

Mass (FAB) m/z: 949 [M+H]$^+$.

(2) Following the same procedure as in Example 3(2) using 8.3 g of the compound obtained in the above (1), there was obtained 6.7 g of the 3-hydroxyl compound.

(3) Following the same procedure as in Example 1(3) for acetylation using 2.20 g of the compound obtained in the above (2) and 0.83 ml (8.8 mmoles) of acetic anhydride, there was obtained 2.47 g of 2'-O-acetyl-11-{2-[N-acetyl-N-(3-pyridylmethyl)-amino]ethyl}amino-11-deoxy-5-O-desosaminyl-6-O-methylerythronolide A 11,12-cyclic carbamate.

Mass (SIMS) m/z: 833 [M+H]$^+$.

(4) Following the same procedure as in Example 2 using 0.81 g (0.97 mmole) of the compound obtained in the above (3), there was obtained 0.37 g (yield: 42%) of the title compound.

Mass (SIMS) m/z: 910 [M+H]$^+$; $^1$H-NMR (500 MHz, DMSO-d$_6$) δ(ppm): 2.02 (s, 3H, —COCH$_3$), 2.22 (s, 6H, N(CH$_3$)$_2$), 2.71 (s, 3H, 6-OMe).

EXAMPLE 63
Synthesis of 11-{2-[N-acetyl-N-(3-pyridylmethyl)amino]ethyl}amino-11-deoxy-3-O-(3-pyridyl)acetyl-5-O-desosaminyl-6-O-methylerythronolide A 11,12-cyclic carbamate Following the same procedure as in Example 1(4) using 0.81 g (0.97 mmole) of the compound obtained in Example 62(3), there was obtained 0.34 g (yield: 39%) of the title compound.

Mass (SIMS) m/z: 910 [M+H]$^+$; $^1$H-NMR (200 MHz, DMSO-d$_6$) δ(ppm): 2.03 (s, 3H, —COCH$_3$), 2.23 (s, 6H, N(CH$_3$)$_2$), 2.73 (s, 3H, 6-OMe).

EXAMPLE 64
Synthesis of 11-{2-[N-tert-butoxycarbonyl-N-(3-pyridylmethyl)amino]ethyl}amino-11-deoxy-3-O-(3-pyridyl)acetyl-5-O-desosaminyl-6-O-methylerythronolide A 11,12-cyclic carbamate (1) To a solution of 2.31 g (3.1 mmoles) of the compound obtained in Example 62(2) in 25 ml of acetone was added 2.0 g (9.2 mmoles) of di-tert-butyldicarbonate, followed by stirring at room temperature for 2 hours. After the reaction, the mixture was diluted with ethyl acetate, and successively washed with a saturated aqueous sodium bicarbonate solution and a saturated aqueous sodium chloride solution. The organic layer was dried over anhydrous magnesium sulfate, followed by evaporation of the solvent under reduced pressure to give 3.57 g of 11-{2-[N-tert-butoxycarbonyl-N-(3-pyridylmethyl)amino]-ethyl}amino-2'-O-(tert-butoxycarbonyl)-11-deoxy-5-O-desosaminyl-6-O-methylerythronolide A 11,12-cyclic carbamate.

(2) Following the same procedure as in Example 1(4) using 1.21 g (1.27 mmoles) of the compound obtained in the above (1), there was obtained 0.73 g of the 3-pyridylacetyl compound. The compound was dissolved in 15 ml of methanol, and stirred overnight. After evaporation of the solvent, purification by silica gel column chromatography (chloroform:methanol:aqueous ammonia=15:1:0.1) gave 0.38 g (yield: 31%) of the title compound.

Mass (SIMS) m/z: 968 [M+H]$^+$; $^1$H-NMR (500 MHz, DMSO-d$_6$, 60° C.) δ(ppm): 1.39 (s, 9H, t-Bu), 2.24 (s, 6H, N(CH$_3$)$_2$), 2.77 (s, 3H, 6-OMe), 3.83 and 3.95 (each d, each 1H, J$_{gem}$=16.5 Hz, —COCH$_2$[3-Pyr.]), 4.41 and 4.53 (each d, each 1H, J$_{gem}$=15.9 Hz, —NCH$_2$[3-Pyr.]), 4.89 (d, 1H, J=11.0 Hz, H-3), 4.89 (d, 1H, J=11.0 Hz, H-3) $^{13}$C-NMR (125 MHz, DMSO-d$_6$, 60° C.) δ(ppm): 27.7 (t-Bu), 37.1 (—COCH$_2$[3-Pyr.]), 40.0 (N(CH$_3$)$_2$), 49.7 (—NCH$_2$[3-Pyr.]), 49.1 (6-OMe), 102.6 (C1'), 156.0 (11,12-carbamate), 170.5 (—COCH$_2$[3-Pyr.]), 173.8 (C1), 215.2 (C9).

EXAMPLE 65

Synthesis of 11-{2-[N-(3-pyridylmethyl)amino]ethyl}amino-11-deoxy-3-O-(3-pyridyl)acetyl-5-O-desosaminyl-6-O-methylerythronolide A 11,12-cyclic carbamate To a solution of 0.17 g (0.18 mmole) of the compound obtained in Example 64 in 3 ml of methylene chloride was added 0.5 ml of trifluoroacetic acid under ice-cooling, followed by stirring for 3 hours. After the reaction, an aqueous sodium hydroxide solution was added to the mixture, followed by extraction with chloroform. The organic layer was dried over anhydrous magnesium sulfate, and the solvent was evaporated under reduced pressure. The residue was purified by silica gel column chromatography (chloroform:methanol: aqueous ammonia=10:1:0.1) to give 0.14 g (yield: 92%) of the title compound.

Mass (SIMS) m/z: 868 [M+H]$^+$; $^1$H-NMR (500 MHz, CDCl$_3$) δ(ppm): 2.28 (s, 6H, N(CH$_3$)$_2$), 3.03 (s, 3H, 6-OMe), 5.03 (d, 1H, J=11.6 Hz, H-3), 5.32 (dd, 1H, J=11.6, 2.4 Hz, H-13) $^{13}$C-NMR (125 MHz, CDCl$_3$) δ(ppm): 40.3 (N(CH$_3$)$_2$), 50.1 (6-OMe), 103.8 (C1'), 158.0 (11,12-carbamate), 170.4 (—COCH$_2$[3-Pyr.]), 174.1 (C1), 215.9 (C9)

EXAMPLE 66

Synthesis of 11-{2-[N-(3-pyridylmethyl)amino]ethyl}amino-11-deoxy-3-O-(2-pyridyl)acetyl-5-O-desosaminyl-6-O-methylerythronolide A 11,12-cyclic carbamate Following the same procedures as in Examples 2 and 65 using 2.15 g (2.3 mmoles) of the compound obtained in Example 64(1), there was obtained 0.10 g of the title compound.

Mass (FAB) m/z: 868 [M+H]$^+$; $^1$H-NMR (500 MHz, CDCl$_3$) δ(ppm): 2.29 (s, 6H, N(CH$_3$)$_2$), 3.02 (s, 3H, 6-OMe), 3.81 and 3.88 (each d, each 1H, J$_{gem}$=13.4 Hz, —NCH$_2$[3-Pyr.]), 3.92 and 3.96 (each d, each 1 E, J$_{gem}$=15.9 Hz, —COCH$_2$[2-Pyr.]), 4.07 (d, 1H, J=6.7 Hz, H-1'), 5.05 (d, 1H, J=11.0 Hz, H-3), 5.32 (dd, 1H, J=11.0, 2.4 Hz, H-13) $^{13}$C-NMR (125 MHz, CDCl$_3$) δ(ppm): 40.3 (N(CH$_3$)$_2$), 50.1 (6-OMe), 103.5 (C1'), 158.0 (11,12-carbamate), 170.5 (—COCH$_2$[2-Pyr.]), 174.3 (C1), 216.0 (C9)

EXAMPLE 67

Synthesis of 11-{2-[N-(2-pyridyl)acetyl-N-(3-pyridylmethyl)amino]ethyl}amino-11-deoxy-3-O-(2-pyridyl)acetyl-5-O-desosaminyl-6-O-methylerythronolide A 11,12-cyclic carbamate Following the same procedure as in Example 2 using 0.64 g (0.85 mmole) of the compound obtained in Example 62(2), 0.78 g (4.50 mmoles) of 2-pyridylacetic acid hydrochloride, 0.86 9 (4.5 mmoles) of 1-(3-dimethylaminopropyl)-3-ethylcarbodiimide hydrochloride and 0.13 g (1.1 mmoles) of 4-dimethylaminopyridine, there was obtained 0.25 g (yield: 30%) of the title compound.

Mass (SIMS) m/z: 987 [M+H]$^+$; $^1$H-NMR (500 MHz, CDCl$_3$) δ(ppm): 2.29 (s, 6H, N(CH$_3$)$_2$), 2.84 (s, 3H, 6-OMe) $^{13}$C-NMR (125 MHz, CDCl$_3$) δ(ppm): 40.3 (N(CH$_3$)$_2$), 103.7 (C1'), 216.1 (C9)

EXAMPLE 68

Synthesis of 11-{2-[N-(2-pyridylacetyl)amino]ethyl}amino-11-deoxy-3-O-(2-pyridyl)acetyl-5-O-desosaminyl-6-O-methylerythronolide A 11,12-cyclic carbamate Following the same procedure as in Example 2 for 2-pyridylacetylation, using 1.04 g (1.6 mmoles) of the compound obtained in Example 38(1), 0.83 g (4.8 mmoles) of 2-pyridylacetic acid hydrochloride, 0.91 g (4.7 mmoles) of 1-(3-dimethylaminopropyl)-3-ethylcarbodiimide hydrochloride and 0.10 g (0.8 mmole) of 4-dimethylaminopyridine, there was obtained 0.56 g (yield: 39%) of the title compound.

Mass (SIMS) m/z: 896 [M+H]$^+$; $^1$H-NMR (500 MHz, CDCl$_3$) δ(ppm): 2.29 (s, 6H, N(CH$_3$)$_2$), 3.04 (s, 3H, 6-OMe), 3.92 and 3.96 (each d, each 1H, J$_{gem}$=15.9 Hz, —COCH$_2$[2-Pyr.]), 4.07 (d, 1H, J=7.3 Hz, H-1'), 5.05 (d, 1H, J=11.0 Hz, H-3), 5.09 (dd, 1H, J=11.0, 2.4 Hz, H-13). $^{13}$C-NMR (125 MHz, CDCl$_3$) δ(ppm): 40.3 (N(CH$_3$)$_2$), 50.3 (6-OMe), 103.6 (C1'), 157.6 (11,12-carbamate), 169.6 and 170.4 (each —COCH$_2$[2-Pyr.]), 174.7 (C1), 215.5 (C9).

EXAMPLE 69

Synthesis of 11-{2-[N-methyl-N-(3-pyridylmethyl)amino]ethyl}amino-11-deoxy-3-O-(2-pyridyl)acetyl-5-O-desosaminylerythronolide A 11,12-cyclic carbamate (1) 20.3 g (23.6 mmoles) of 10,11-anhydro-2',4"-bis-O-trimethylsilylerythromycin A was dissolved in 400 ml of 0.5N aqueous hydrochloric acid solution, and stirred at room temperature for 7 hours. After the reaction, the mixture was made basic with an aqueous sodium hydroxide solution and extracted with chloroform. The organic layer was dried over anhydrous magnesium sulfate, and the solvent was evaporated under reduced pressure. The residue was recrystallized from 2-propanol/n-hexane to give 7.3 g (yield: 55%) of 10,11-anhydro-5-O-desosaminylerythronolide A as the first crystals.

Mass (SIMS) m/z: 558 [M+H]$^+$; $^1$H-NMR (500 MHz, CDCl$_3$) δ(ppm): 2.06 (d, 3H, J=1.5 Hz, 10Me), 2.28 (s, 6H, N(CH$_3$)$_2$), 4.43 (d, 1H, J=7.4 Hz, H-1'), 4.99 (dd, 1H, J=11.0, 1.8 Hz, H-13), 6.44 (d, 1H, J=1.5 Hz, H-11) $^{13}$C-NMR (125 MHz, CDCl$_3$) δ(ppm): 12.8 (10Me), 40.2 (N(CH$_3$)$_2$), 106.2 (C1'), 139.6 (C10), 141.1 (C11), 177.0(C1), 207.9(C9)

(2) Following the same procedure as in Example 1(3) using 9.28 g (16.6 mmoles) of the compound obtained in the above (1), there was obtained 9.70 g of the 2'-O-acetyl compound.

(3) To a solution of 9.70 g of the compound obtained in the above (2) in 200 ml of methylene chloride were successively added 2.8 g (33.3 mmoles) of sodium bicarbonate, 4.3 g (25 mmoles) of 2-pyridylacetic acid hydrochloride, 4.8 g (25 mmoles) of 1-(3-dimethylaminopropyl)-3-ethylcarbodiimide hydrochloride and 3.05 g (25 mmoles) of 4-dimethylaminopyridine under icecooling, followed by stirring at room temperature for 1.5 hours. After the reaction, a saturated aqueous sodium bicarbonate solution was added to the mixture, followed by extraction with chloroform. The organic layer was dried over anhydrous magnesium sulfate under reduced pressure, and purification by silica gel column chromatography (acetone:n-hexane:triethylamine= 10:10:0.2) gave 8.11 g (yield: 68%) of 10,11-anhydro-2'-O-acetyl-3-O-(2-pyridyl)acetyl-5-O-desosaminylerythronolide A.

Mass (SIMS) m/z: 719 [M+H]$^+$; $^1$H-NMR (500 MHz, CDCl$_3$) δ(ppm): 2.02 (s, 3H, 10Me), 2.10 (s, 3H, —COCH$_3$), 2.27 (s, 6H, N(CH$_3$)$_2$), 3.88 and 3.94 (each d, each 1H, J$_{gem}$=15.9 Hz, —COCH$_2$[2-Pyr.]), 4.27 (d, 1H, J=7.9 Hz, H-1'), 5.24 (dd, 1H, J=11.0, 1.8 Hz, H-13), 5.31 (d, 1H, J=7.3 Hz, H-3), 6.37 (s, 1H, H-11) $^{13}$C-NMR (125 MHz, CDCl$_3$) δ(ppm): 40.7 (N(CH$_3$)$_2$), 101.3 (C1'), 140.1 (C11), 140.7 (C10), 169.8 (—COCH$_3$), 170.3 (—COCH$_2$[2-Pyr.]), 173.2(C1), 206.5(C9)

(4) 1.34 g (1.87 mmoles) of the compound obtained in the above (3) was dissolved in 18 ml of tetrahydrofuran and 12 ml of N,N-dimethylformamide, and 0.22 g (5.5 mmoles) of sodium hydride was added thereto under ice-cooling, followed by stirring under ice-cooling for 2 hours. After the reaction, the mixture was diluted with ethyl acetate, and successively washed with distilled water and a saturated aqueous sodium chloride solution. The organic layer was dried over anhydrous magnesium sulfate, and evaporation of the solvent under reduced pressure gave 1.42 g of the 12-O-imidazolylcarbonyl compound. The compound was dissolved in 30 ml of acetonitrile, and 3.09 g (18.7 mmoles) of 2-[N-methyl-N-(3-pyridylmethyl)amino]ethylamine was added thereto, followed by stirring at room temperature for 2 days. After the reaction, the solvent was evaporated, and the residue was dissolved in 80 ml of methanol and stirred overnight. After the reaction, the solvent was evaporated, and the residue was purified by silica gel column chromatography (chloroform:methanol:aqueous ammonia= 20:1:0.1) to give 0.46 g (yield: 28%) of the title compound.

Mass (FAB) m/z: 868 [M+H]$^+$; $^1$H-NMR (500 MHz, DMSO-d$_6$) δ(ppm): 2.05 (s, 3H, NCH$_3$), 2.24 (s, 6H, N(CH$_3$)$_2$), 3.38 and 3.59 (each d, each 1H, J$_{gem}$=13.4 Hz, —NCH$_2$[3-Pyr.]), 3.84 (s, 1H, H-11), 3.99 (d, 1H, J=7.0 Hz, H-1'), 3.93 and 4.06 (each d, each 1H, J$_{gem}$=16.2 Hz, —COCH$_2$[2-Pyr.]), 5.09 (dd, 1H, J=8.2, 4.0 Hz, H-13), 5.12 (d, 1H, J=11.0 Hz, H-3) $^{13}$C-NMR (125 MHz, DMSO-d$_6$) δ(ppm): 40.4 (N(CH$_3$)$_2$), 41.4 (NCH$_3$), 58.3 (—NCH$_2$[3-Pyr.]), 102.4 (C1'), 155.4 (11,12-carbamate), 170.3 (—COCH$_2$[2-Pyr.]), 173.3 (C1), 215.3 (C9)

EXAMPLE 70

Synthesis of 11-{2-[N-methyl-N-(3-pyridylmethyl)amino] ethyl}amino-11-deoxy-3-O-(4-methoxyphenylamino) carbonyl-5-O-desosaminyl-6-O-methylerythronolide A 11,12-cyclic carbamate (1) To a solution of 11.0 g (16.7 mmoles) of the compound obtained in Example 38(1) in 150 ml of methylene chloride were successively added 1.97 g (18.4 mmoles) of nicotinealdehyde and 7.08 g (33.4 mmoles) of sodium triacetoxyborohydride at room temperature, followed by stirring for an hour. Then, 2.7 ml (33.4 mmoles) of 37% aqueous formaldehyde solution and 3.54 g (16.7 mmoles) of sodium triacetoxyborohydride were added to the mixture, followed by stirring for 2.5 hours. The reaction solution was diluted with chloroform and successively washed with an aqueous sodium hydroxide solution and a saturated aqueous sodium chloride solution, and the organic layer was dried over anhydrous magnesium sulfate. Evaporation of the solvent under reduced pressure gave 14.1 g of 11-{2-[N-methyl-N-(3-pyridylmethyl)amino]ethyl}amino-11-deoxy-5-O-desosaminyl-6-O-methylerythronolide A 11,12-cyclic carbamate.

(2) Carrying out the same reaction as in Example 1(3) using 14.1 g of the compound obtained in the above (1), there was obtained 14.4 g of the 2'-O-acetyl compound.

(3) To a solution of 0.50 g (0.62 mmole) of the compound obtained in the above (2) in 15 ml of methylene chloride was added 0.50 ml (6.2 mmoles) of pyridine. 0.092 g (0.31 imole) of triphosgene was added thereto under ice-cooling, followed by stirring for 1.5 hours. Then, 0.38 g (3.1 mmoles) of p-anisidine was added to the mixture, followed by stirring for further an hour. To the reaction solution was added water to decompose excess triphosgene, and the mixture was diluted with chloroform and successively washed with a saturated aqueous ammonium chloride solution and a saturated aqueous sodium chloride solution. The organic layer was dried over anhydrous magnesium sulfate, the solvent was evaporated under reduced pressure, and the resulting residue was dissolved in methanol, followed by heating under reflux for 3 hours. After allowing to stand for cooling, the solvent was evaporated under reduced pressure, and the residue was purified by silica gel column chromatography (acetone:hexane:triethylamine=10:10:0.2) to give 0.26 g (yield: 46%) of the title compound.

Mass (IonSpray) m/z: 912.5 [M+H]$^+$; $^1$H-NMR (500 MHz, CDCl$_3$) δ(ppm): 0.74 (t, 3H, J=7.3 Hz, H-15), 2.17 (s, 6H, 3'-N(CH$_3$)$_2$), 2.20 (s, 3H, NCH$_3$), 3.06(s, 3H, 6-OCH$_3$), 3.78 (s, 3H, ArOCH$_3$), 4.95 (d, 1H, J=11.3 Hz, H-3), 5.23 (dd, 1H, J=11.0, 2.1 Hz, H-13), 6.98 (brs, 1H, NH) $^{13}$C-NMR (125 MHz, CDCl$_3$) δ(ppm): 55.6 (ArOCH$_3$), 153.5 (3-carbamate)

EXAMPLE 71

Synthesis of 11-{2-[N-methyl-N-(3-pyridylmethyl)amino] ethyl}amino-11-deoxy-3-O-(2-methoxyphenylamino) carbonyl-5-O-desosaminyl-6-O-methylerythronolide A 11,12-cyclic carbamate Carrying out the same reaction as in Example 70(3) using 0.50 g (0.62 mmole) of the compound obtained in Example 70(2) and 0.38 g (3.10 mmoles) of o-anisidine, there was obtained 0.23 g (yield: 41%) of the title compound.

Mass (IonSpray) m/z: 912.5 [M+H]$^+$; $^1$H-NMR (500 MHz, CDCl$_3$) δ(ppm): 0.75 (t, 3H, J=7.3 Hz, H-15), 2.15 (s, 6H, 3'-N(CH$_3$)$_2$), 2.20 (s, 3H, NCH$_3$), 3.08 (s, 3H, 6-OCH$_3$), 3.89 (s, 3H, ArOCH$_3$), 4.99 (d, 1H, J=11.6 Hz, H-3), 5.25 (dd, 1H, J=11.0, 2.1 Hz, H-13), 7.39 (brs, 1H, NH) $^{13}$C-NMR (125 MHz, CDCl$_3$) 55.6 (ArOCH$_3$), 153.2 (3-carbamate)

EXAMPLE 72

Synthesis of 11-{2-[N-methyl-N-(3-pyridylmethyl)amino] ethyl}amino-11-deoxy-3-O-(3-methoxyphenylamino) carbonyl-5-O-desosaminyl-6-O-methylerythronolide A 11,12-cyclic carbamate Carrying out the same reaction as in Example 70(3) using 0.50 g (0.62 mmole) of the compound obtained in Example 70(2) and 0.38 g (3.10 mmoles) of m-anisidine, there was obtained 0.20 g (yield: 35%) of the title compound.

Mass (IonSpray) m/z: 912.5 [M+H]$^+$; $^1$H-NMR (500 MHz, CDCl$_3$) δ(ppm): 0.74 (t, 3H, J=7.3 Hz, H-15), 2.17 (s, 6H, 3'-N(CH$_3$)$_2$), 2.20 (S, 3H, NCH$_3$), 3.07 (s, 3H, 6-OCH$_3$), 3.79 (s, 3H, ArOCH$_3$), 4.97 (d, 1H, J=10.9 Hz, H-3), 5.24 (dd, 1H, J=11.0, 1.9 Hz, H-13), 8.13 (brs, 1H, NH) $^{13}$C-NMR (125 MHz, CDCl$_3$) δ(ppm): 55.2 (ArOCH$_3$), 153.4 (3-carbamate)

EXAMPLE 73
Synthesis of 11-{2-[N-methyl-N-(3-pyridylmethyl)amino]ethyl}amino-11-deoxy-3-O-(phenylamino)carbonyl-5-O-desosaminyl-6-O-methylerythronolide A 11,12-cyclic carbamate Carrying out the same reaction as in Example 70(3) using 0.50 g (0.62 mmole) of the compound obtained in Example 70(2) and 0.29 g (3.10 mmoles) of aniline, there was obtained 0.22 g (yield: 40%) of the title compound.

Mass (IonSpray) m/z: 882.4 [M+H]$^+$; $^1$H-NMR (500 MHz, CDCl$_3$) δ(ppm): 0.74 (t, 3H, J=7.3 Hz, H-15), 2.15 (s, 6H, 3'-N(CH$_3$)$_2$), 2.20 (s, 3H, NCH$_3$), 3.07 (s, 3H, 6-OCH$_3$), 4.97 (d, 1H, J=10.9 Hz, H-3), 5.23 (dd, 1H, J=11.0, 2.5 Hz, H-13), 7.05 (t, 1H, J=7.5 Hz, Ar-H), 7.30 (t, 2H, J=7.5 Hz, Ar-H), 7.46 (m, 2H, Ar-H), 7.72 (brs, 1H, NH) $^{13}$C-NMR (125 MHz, CDCl$_3$) δ(ppm): 153.4 (3-carbamate)

EXAMPLE 74
Synthesis of 11-{2-[N-methyl-N-(3-pyridylmethyl)amino]ethyl}amino-11-deoxy-3-O-(3-methylphenylamino)carbonyl-5-O-desosaminyl-6-O-methylerythronolide A 11,12-cyclic carbamate Carrying out the same reaction as in Example 70(3) using 0.50 g (0.62 mnmole) of the compound obtained in Example 70(2) and 0.33 g (3.10 mmoles) of m-toluidine, there was obtained 0.18 g (yield: 32%) of the title compound.

Mass (IonSpray) m/z: 896.4 [M+H]$^+$; $^1$H-NMR (500 MHz, CDCl$_3$) δ(ppm): 0.74 (t, 3H, J=7.3 Hz, H-15), 2.16 (s, 6H, 3'-N(CH$_3$)$_2$), 2.20 (s, 3H, NCH$_3$), 2.33 (s, 3H, ArCH$_3$), 3.07 (s, 3H, 6-OCH$_3$), 4.96 (d, 1H, J=11.3 Hz, H-3), 5.23 (dd, 1H, J=11.1, 2.1 Hz, H-13), 7.46 (brs, 1H, NH) $^{13}$C-NMR (125 MHz, CDCl$_3$) δ(ppm): 21.5 (ArCH$_3$), 153.3 (3-carbamate)

EXAMPLE 75
Synthesis of 11-{2-[N-methyl-N-(3-pyridylmethyl)amino]ethyl}amino-11-deoxy-3-O-(8-quinolineamino)carbonyl-5-O-desosaminyl-6-O-methylerythronolide A 11,12-cyclic carbamate Carrying out the same reaction as in Example 70(3) using 0.50 g (0.62 mmole) of the compound obtained in Example 70(2) and 0.45 g (3.1 mmoles) of 8-aminoquinoline, there was obtained 0.08 g (yield: 14%) of the title compound. Mass (IonSpray) m/z: 933 [M+H]$^+$; $^1$H-NMR (300 MHz, CDCl$_3$) δ(ppm): 0.76 (t, 3H, J=7.3 Hz, H-15), 1.92 (s, 6H, 3'-N(CH$_3$)$_2$), 2.21 (s, 3H, NCH$_3$), 3.11 (s, 3H, 6-OCH$_3$), 5.08 (d, 1H, J=11.3 Hz, H-3), 5.26 (dd, 1H, J=11.0, 2.3 Hz, H-13), 7.45–7.59 (m, 3H, quinolyl-H), 8.18 (dd, 1H, J=8.3, 1.6 Hz, quinolyl-H), 8.84 (dd, 1H, J=4.1, 1.6 Hz, quinolyl-H), 9.32 (s, 1H, quinolyl-H)

EXAMPLE 76
Synthesis of 11-{2-[N-methyl-N-(3-pyridylmethyl)amino]ethyl}amino-11-deoxy-3-O-(2-pyridylmethoxy)carbonyl-5-O-desosaminyl-6-O-methylerythronolide A 11,12-cyclic carbamate Carrying out the same reaction as in Example 70(3) using 0.50 g (0.62 nmmole) of the compound obtained in Example 70(2) and 0.34 g (3.10 mmoles) of 2-pyridinemethanol, there was obtained 0.08 g (yield: 14%) of the title compound.

$^1$H-NMR (300 MHz, CDCl$_3$) δ(ppm): 0.74 (t, 3H, J=7.3 Hz, H-15), 2.19 (s, 3H, NCH$_3$), 2.23 (s, 6H, 3'N(CH$_3$)$_2$), 3.04 (s, 3H, 6-OCH$_3$), 4.84 (d, 1H, J=11.1 Hz, H-3), 5.20 (d, 1H, J=13.2 Hz, OCH$_2$Py), 5.22 (dd, 1H, J=10.8, 2.1 Hz, H-13), 5.38 (d, 1H, J=13.2 Hz, OCH$_2$Py)

EXAMPLE 77
Synthesis of 11-{2-[N-methyl-N-(3-pyridylmethyl)amino]ethyl}amino-11-deoxy-3-O-(4-methoxyphenoxy)carbonyl-5-O-desosaminyl-6-O-methylerythronolide A 11,12-cyclic carbamate Carrying out the same reaction as in Example 70(3) using 0.50 g (0.62 mmole) of the compound obtained in Example 70(2) and 0.39 g (3.10 mmoles) of p-methoxyphenol, there was obtained 0.15 g (yield: 26%) of the title compound.

Mass (SIMS) m/z: 913 [M+H]$^+$; $^1$H-NMR (300 MHz, CDCl$_3$) δ(ppm): 0.75 (t, 3H, J=7.3 Hz, H-15), 2.19 (s, 3H, NCH$_3$), 2.26 (s, 6H, 3'-N(CR$_3$)$_2$), 3.03 (s, 3H, 6-OCH$_3$), 3.80 (s, 3H, ArOCH$_3$), 4.87 (d, 1H, J=11.2 Hz, H-3), 5.22 (dd, 1H, J=11.0, 2.1 Hz, H-13)

EXAMPLE 78
Synthesis of 11-{2-[N-methyl-N-(3-pyridylmethyl)amino]ethyl}amino-11-deoxy-3-O-(o-nitrophenyl)-5-O-desosaminyl-6-O-methylerythronolide A 11,12-cyclic carbamate (1) To a solution of 5.0 g (8.5 imoles) of 5-O-desosaminyl-6-O-methylerythronolide A in 30 ml of tetrahydrofuran was added 3.0 g (21 mmoles) of 2-fluoronitrobenzene. 0.30 g (13 mmoles) of sodium hydride was added to the mixture under ice-cooling, followed by stirring for 0.5 hour. The temperature was raised to room temperature, followed by stirring overnight. After the reaction, the reaction solution was cooled on ice, diluted with ethyl acetate and separated with water. The organic layer was washed with a saturated aqueous sodium chloride solution and dried over anhydrous magnesium sulfate. After evaporation of the solvent under reduced pressure, the residue was purified by silica gel column chromatography (chloroform:methanol=98:2) to give 1.6 g (yield: 27%) of 3-O-(2-nitrophenyl)-5-O-desosaminyl-6-O-methylerythronolide A.

(2) 1.6 g (2.3 mmoles) of the compound obtained in the above (1) was dissolved in 20 ml of acetone, and 0.25 ml (2.7 mmoles) of acetic anhydride was added thereto at room temperature, followed by stirring overnight. After evaporation of the solvent under reduced pressure, the residue was diluted with ethyl acetate, and successively washed with a saturated aqueous sodium bicarbonate solution and a saturated aqueous sodium chloride solution. The organic layer was dried over anhydrous magnesium sulfate, and the solvent was evaporated under reduced pressure to give 1.7 g of the 2'-O-acetyl compound.

(3) To a solution of 1.7 g (2.3 mmoles) of the compound obtained in the above (2) in 20 ml of methylene chloride was added 1.8 ml (23 mmoles) of pyridine. 0.67 g (2.3 mmoles) of triphosgene was added thereto under ice-cooling, followed by stirring for 2 hours. To the reaction solution was added water to decompose excess triphosgene, and the mixture was diluted with chloroform and successively washed with water and a saturated aqueous sodium chloride solution, and dried over anhydrous magnesium sulfate. After evaporation of the solvent under reduced pressure, the resulting residue was dissolved in 15 ml of N,N-dimethylformamide, and 0.39 g (3.4 mmoles) of 1,1,3,3-tetramethylguanidine was added thereto, followed by stirring at 100° C. for 3 hours. After allowing to stand for cooling, the mixture was diluted with ethyl acetate and separated with water. The organic layer was successively washed with water and a saturated aqueous sodium chloride solution, and dried over anhydrous magnesium sulfate. Evaporation of the solvent under reduced pressure gave 1.6 g of 10,11-anhydro-3-O-(o-nitrophenyl)-5-O-desosaminyl-6-O-methylerythronolide A.

(4) To a solution of 1.6 g (2.2 mmoles) of the compound obtained in the above (3) in 20 ml of 1,2-dichloroethane were added 4.1 g (26 mmoles) of 1,1'-carbonyldiimidazole and 1.6 g (12 mmoles) of 4-dimethylaminopyridine, followed by heating under reflux for an hour. After allowing to stand for cooling, the reaction solution was diluted with chloroform, and separated with a saturated aqueous ammonium chloride solution. The organic layer was successively washed with water and a saturated aqueous sodium chloride solution, and dried over anhydrous magnesium sulfate. The solvent was evaporated under reduced pressure, and the residue was purified by silica gel column chromatography to give 1.1 g (yield: 64%) of the 12-O-imidazolylcarbonyl compound.

(5) To a solution of 0.5 g (0.63 mmole) of the compound obtained in the above (4) in 5 ml of acetonitrile was added 1.0 g (6.3 mmoles) of N-methyl-N-(3-pyridylmethyl) ethylenediamine, followed by stirring at room temperature overnight. The reaction solution was diluted with chloroform, successively washed with a saturated aqueous ammonium chloride solution and a saturated aqueous sodium chloride solution, and dried over anhydrous magnesium sulfate. The solvent was evaporated under reduced pressure, and the resulting residue was dissolved in 20 ml of methanol, and heated under reflux for 2 hours. After allowing to stand for cooling, the solvent was evaporated under reduced pressure, and the residue was purified by silica gel column chromatography (chloroform:methanol:aqueous ammonia=30:1:0.1) to give 0.31 g (yield: 56%) of the title compound.

Mass (SIMS) m/z: 884 [M+H]$^+$; $^1$H-NMR (300 MHz, CDCl$_3$) δ(ppm): 0.74 (dd, 3H, J=7.6, 6.0 Hz, H-15), 2.22 (s, 9H, NCH$_3$ and 3'-N(CH$_3$)$_2$), 3.08 (s, 3H, 6-OCH$_3$), 4.60 (d, 1H, J=10.8 Hz, H-3), 5.21 (dd, 1H, J=11.0, 2.3 Hz, H-13), 7.03 (m, 1H, Ar-H), 7.28 (m, 1H, Ar-H), 7.55 (m, 1H, Ar-H), 7.75 (m, 1H, Ar-H)

EXAMPLE 79
Synthesis of 11-[2-(1-piperazinyl)ethyl]amino-11-deoxy-3-O-(2-pyridyl)acetyl-5-O-desosaminyl-6-O-methylerythronolide A 11,12-cyclic carbamate (1) Carrying out the same reaction as in Example 78(3) using 53.56 g (0.085 mole) of 2'-O-acetyl-5-O-desosaminyl-6-O-methylerythronolide A, there was obtained 50.27 g (yield: 97%) of 10,11-anhydro-2'-O-acetyl-5-O-desosaminyl-6-O-methylerythronolide A.

(2) Carrying out the same esterification at the 3-position as in Example 1(4) using 50.27 g (0.082 mole) of the compound obtained in the above (1) and 42.65 g (0.25 mole) of 2-pyridylacetic acid hydrochloride, there was obtained 41.95 g (yield: 70%) of 10,11-anhydro-2'-O-acetyl-3-O-(2-pyridyl)acetyl-5-O-desosaminyl-6-O-methylerythronolide A.

(3) To a solution of 31.01 g (0.042 mole) of the compound obtained in the above (2) in 300 ml of a mixture of N,N-dimethylformamide and tetrahydrofuran (3:2) was added 20.58 g (0.126 mole) of N,N'-carbonyldiimidazole at room temperature, then 3.38 g (0.084 mole) of 60% sodium hydride under ice-cooling, followed by stirring under ice-cooling for 40 minutes. To the reaction solution was added water, followed by extraction with ethyl acetate. The ethyl acetate layer was washed with water and a saturated aqueous sodium chloride solution, and dried over anhydrous magnesium sulfate. Evaporation of the solvent gave 32.71 g (yield; 93%) of 10,11-anhydro-2'-O-acetyl-12-O-imidazolylcarbonyl-3-O-(2-pyridyl)acetyl-5-O-desosaminyl-6-O-methylerythronolide A.

(4) To a solution of 1.00 g (1.21 mmoles) of the compound obtained in the above (3) in 10 ml of acetonitrile was added 1.56 g of N-(2-aminoethyl)piperazine at room temperature, followed by stirring for a day. To the reaction solution was added an aqueous ammonium chloride solution, followed by extraction with ethyl acetate. The ethyl acetate layer was washed with water and a saturated aqueous sodium chloride solution, and dried over anhydrous magnesium sulfate, and the solvent was evaporated. The residue was dissolved in 20 ml of methanol, and stirred at room temperature for 3 days, and the solvent was evaporated. The residue was purified by silica gel column chromatography (eluant; chloroform:methanol:aqueous ammonia=19:1:0.1~9:1:0.1) to give 0.47 g (yield: 46%) of the title compound.

MS (IonSpray); m/z 884 [M+H]$^+$; $^1$H-NMR (300 MHz, CDCl$_3$) δ(ppm): 2.29 (6H, s, N(CH$_3$)$_2$), 3.03 (3H, s, 6-OCH$_3$), 5.06 (1H, d, J=11.3 Hz, 3-H), 5.31 (1H, dd, J=11.0, 2.5 Hz, 13-H), 7.18–7.24 (1H, m, Py), 7.33–7.39 (1H, m, Py), 7.64–7.73 (1H, m, Py), 8.49–8.56 (1H, m, Py). $^{13}$C-NMR (75 MHz, CDCl$_3$) δ(ppm): 40.4 (Q, N(CH$_3$)$_2$), 50.2 (Q, 6-O CH$_3$), 216.2 (S, C1).

EXAMPLE 80
Synthesis of 11-{2-[N-methyl-N-(3-pyridylmethyl)amino]propyl}amino-11-deoxy-3-O-(2-pyridyl)acetyl-5-O-desosaminyl-6-O-methylerythronolide A 11,12-cyclic carbamate (1) Carrying out the same reaction as in Example 79(4) using 3.0 g (3.41 mmoles) of the compound obtained in Example 79(3) and 2.9 ml (34.1 mmoles) of 1,2-diaminopropane, there was obtained 1.1 g of 11-(2-aminopropyl)amino-11-deoxy-3-O-(2-pyridyl)acetyl-5-O-desosaminyl-6-O-methylerythronolide A 11,12-cyclic carbamate.

(2) Carrying out the same reaction as in Example 3(1) using 1.1 g (1.17 mmoles) of the compound obtained in the above (1), and then carrying out deacetylation at the 2'-position by heating under reflux in methanol, there was obtained 1.0 g of the title compound.

MS (SIMS); m/z 896 [M+H]$^+$; $^1$H-NMR (300 MHz, CDCl$_3$) δ(ppm): 2.16 (3H, s, NCH$_3$), 2.29 (6H, s, N(CH$_3$)$_2$), 3.03 (3H, s, 6-OCH$_3$)

EXAMPLE 81
Synthesis of 11-{2-[N-methyl-N-(3-pyridylmethyl)amino]ethyl}amino-11-deoxy-3-O-(2-pyridyl)acetyl-5-O-desosaminyl-6-O-cinnamylerythronolide A 11,12-cyclic carbamate (1) 22.9 g (0.022 mole) of 2',4"-O-bis-(trimethylsilyl) erythromycin A 9-{O-[1-(1-methylethoxy)-cyclohexyl]oxime} described in U.S. Pat. No. 4,990,602 was dissolved in 230 ml of dimethyl sulfoxide-tetrahydrofuran (1:1), and then 13.1 g of cinnamyl bromide and 2.59 g of 96% potassium hydroxide were added thereto under ice-cooling, followed by stirring under ice-cooling for 1.5 hours. After the reaction, 5 ml of 50% aqueous dimethylamine solution was added to the mixture, followed by stirring at room temperature for 30 minutes. Water was added to the mixture, followed by extraction with hexane. The hexane layer was washed with a saturated aqueous sodium chloride solution and dried over anhydrous magnesium sulfate, and the hexane was evaporated. To a solution of the resulting residue in 150 ml of ethanol were added 2.83 ml of 90% formic acid and 150 ml of water at room temperature, the mixture was heated under reflux for an hour, and then 16.1 g of sodium hydrogen sulfite was added thereto, followed by heating under reflux for further 2 hours. The reaction solution was concentrated, and adjusted to pH 11 with 2N aqueous sodium hydroxide solution under ice-cooling. Water was added to the mixture, followed by extraction with ethyl acetate. The ethyl acetate layer was washed with a saturated aqueous sodium chloride solution and dried over anhydrous magnesium sulfate, and the ethyl acetate was evaporated. The resulting residue was purified by silica gel column chromatography (eluant; chloroform:methanol:aqueous ammonia=94:6:0.6-9:1:0.1) to give 7.76 g of 6-O-cinnamylerythromycin A.

MS (FAB) m/z; 850 [M+H]$^+$; $^1$H-NMR (300 MHz, CDCl$_3$) δ(ppm): 2.29 (6H, s, N(CH$_3$)2), 3.34 (3H, s, OCH$_3$), 4.00, 4.20 (each 1H, each dd, J=4.7, 10.9 Hz, OC H$_2$CH=CHPh), 6.32 (1H, ddd, J=4.7, 10.9, 15.7 Hz, OCH$_2$CH=CHPh), 6.47 (1H, d, J=15.7 Hz, OCH$_2$CH=C HPh)

(2) To a solution of 7.00 g (8.23 mmoles) of the compound obtained in the above (1) in 7 ml of ethanol was added 70 ml of 1N hydrochloric acid, followed by stirring at room temperature for 3.5 hours. The reaction solution was extracted with chloroform, and the chloroform layer was successively washed with dil. hydrochloric acid, an aqueous sodium hydroxide solution and a saturated aqueous sodium chloride solution, and dried over anhydrous magnesium sulfate. After evaporation of the solvent, the resulting residue was dissolved in 30 ml of acetone, and 1.26 g of acetic anhydride was added thereto at room temperature, followed by stirring at room temperature for 1.5 hours. After evaporation of the acetone, the residue was extracted with ethyl acetate, washed with a saturated aqueous sodium bicarbonate solution and a saturated aqueous sodium chloride solution, and dried over anhydrous magnesium sulfate. After evaporation of the ethyl acetate, the residue was purified by silica gel column chromatography (eluant; acetone:hexane:triethylamine=6:10:0.2) to give 4.2 g of 2'-O-acetyl-5-O-desosaminyl-6-O-cinnamylerythronolide A.

(3) Carrying out the same reaction as in Example 2 using 0.49 g (0.7 mmole) of the compound obtained in the above (2), and then crystallizing from dichloromethane-isopropyl ether, there was obtained 0.30 g of 3-O-(2-pyridyl)acetyl-5-O-desosaminyl-6-0-cinnamylerythronolide A.

MS (FAB) m/z; 811 [M+H]$^+$; $^1$H-NMR (300 MHz, CDCl$_3$) δ(ppm): 2.28 (6H, s, N(CH$_3$)$_2$), 5.12 (1H, d, 3-H) $^{13}$C-NMR (75 MHz, CDCl$_3$) δ(ppm): 40.2 (Q. N(CH$_3$)$_2$), 170.4 (S, 3-OCO-), 173.3 (C1), 219.5 (C9).

(4) Carrying out the same reactions as in Examples 78(2), 78(3), 79(3), 1(1) and 3(1) successively, using 0.75 g of the compound obtained in the above (3), there was obtained 0.5 g of the title compound.

MS (FAB) m/z; 984 [M+H]$^+$; $^1$H-NMR (300 MHz, CDCl$_3$) δ(ppm): 2.01 (3H, s, NCH$_3$), 2.30 (6H, s, N(CH$_3$)$_2$).

EXAMPLE 82

Synthesis of 11-{2-[1,2-bis(ethoxycarbonyl)vinylamino] ethyl}amino-11-deoxy-3-O-(2-pyridyl)acetyl-5-O-desosaminyl-6-O-methylerythronolide A 11,12-cyclic carbamate To a solution of 0.5 g (0.64 mmole) of the compound obtained in Example 38(3) in 20 ml of methylene chloride was added 0.11 ml (0.71 mmole) of diethylacetylenedicarboxylate at room temperature, followed by reaction for 5 hours. After evaporation of the solvent under reduced pressure, the resulting residue was purified by silica gel column chromatography (eluant; chloroform:methanol:aqueous ammonia=9:1:0.1) to give 366 mg of the title compound as a yellow foam.

MS (FAB) m/z; 947 [M+H]$^+$.

EXAMPLE 83

Synthesis of 11-{2-[N-(3-quinolylmethyl)amino] ethyl}amino-11-deoxy-3-O-(2-pyridyl)acetyl-5-O-desosaminyl-6-O-methylerythronolide A 11,12-cyclic carbamate Following the same procedure as in Example 50 using a solution of 1.0 g (1.28 mmoles) of the compound obtained in Example 38(3) in 20 ml of methylene chloride and 0.24 g (1.55 mmoles) of 3-quinolinecarboxaldehyde in place of 2-hydroxy-4-methoxybenzaldehyde, there was obtained 0.35 g (yield: 32%) of the title compound.

MS (IonSpray) m/z; 918.5 [M+H]$^+$;.

Experiment [In vitro Antibacterial Activity]

The in vitro antibacterial activity of the compound obtained in Example 4 as an example of the compound of the present invention against various experimental bacteria was measured using sensitive disc media (produced by Eiken Chemical Co.) according to the MIC measuring method specified by the Japan Society of Chemotherapy. Clarithromycin was used as a comparative drug. The results are expressed as MIC value (Minimum Inhibitory Concentration, μg/ml), and shown in Table 1. The compound obtained in Example 4 shows to have a strong antibacterial activity not only against erythromycin-sensitive bacteria but also erythromycin-resistant bacteria.

TABLE 1

In Vitro Antibacterial Activity: MIC (μg/ml)

| Microorganism/Compound | Compound of Example 4 | Comparative drug |
|---|---|---|
| S. aureus 209P-JC | 0.10 | 0.10 |
| S. aureus Smith | 0.20 | 0.20 |
| S. aureus J-109 | >100 | >100 |
| S. aureus B1 | 0.39 | >100 |
| S. pneumoniae IID 553 | 0.10 | 0.10 |
| S. pneumoniae BM 210 | 0.39 | 1.56 |
| S. pneumoniae BM 205 | 0.39 | >100 |

Industrial Applicability

The compounds of the present invention have an antibacterial activity against not only erythromycin-sensitive bacteria but also erythromycin-resistant bacteria. Therefore, the compounds of the present invention are useful as antibacterial agents for the treatment of bacterially infectious diseases in human beings and animals (including farm animals).

What is claimed is:

1. An erythrornycin A derivative represented by Formula (I):

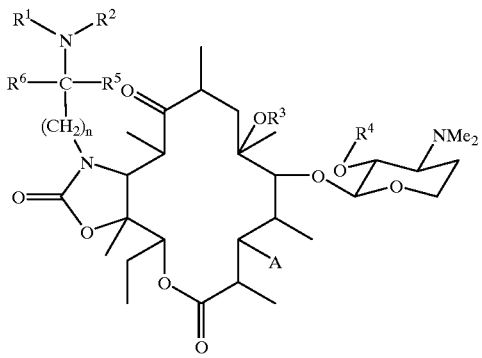

wherein n is an integer of from 1 to 4, $R^1$ is a group represented by the formula:

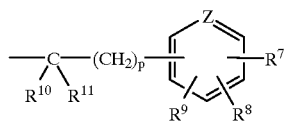

wherein p is 0 or 1, Z is a nitrogen atom or CH; $R^7$, $R^8$ and $R^9$ are each a hydrogen atom, a halogen atom, an alkyl group having 1 to 5 carbon atoms, a nitro group, an amino group, an acetylamino group, an amino group substituted by 1 or 2 alkyl groups having 1 to 3 carbon atoms, a hydroxyl group, a cyano group, an alkyl group having 1 to 3 carbon atoms substituted by 1 to 3 halogen atoms, an alkoxy group having 1 to 5 carbon atoms or a phenyl group, or $R^7$ and $R^8$ are attached to the carbon atoms which are attached side by side, and together form a methylenedioxy group, or $R^7$ and $R^8$ are attached to the carbon atoms which are attached side by side, and together with the carbon atoms to which they attached form a benzene ring, $R^{10}$ and $R^{11}$ are each a hydrogen atom, or $R^{10}$ and $R^{11}$ together form an oxo group, a group represented by the formula:

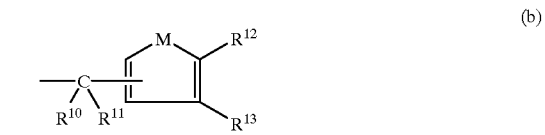

wherein $R^{10}$ and $R^{11}$ are as defined above, M is an oxygen atom, a sulfur atom, —$NCH_3$ or —NH, or $R^{12}$ and $R^{13}$ are each a hydrogen atom, or $R^{12}$ and $R^{13}$ together with the carbon atoms to which they are attached form a benzene ring, (c) a pyridylacetyl group, (d) a cycloalkylmethyl group having 4 to 8 carbon atoms or (e) a 1,2-bis(ethoxy-carbonyl) vinyl group, $R^2$ is the same group as defined for $R^1$, a hydrogen atom, an alkyl group having 1 to 5 carbon atoms, an alkanoyl group having 2 to 6 carbon atoms or an alkoxycarbonyl group having 2 to 6 carbon atoms, $R^1$ and $R^2$ together form a group of the formula: =CH—$R^{14}$ wherein $R^{14}$ is a phenyl group, a phenyl group substituted by nitro group(s), cyano group(s) or alkyl group(s) having 1 to 3 carbon atoms substituted by 1 to 3 halogen atoms, or an imidazolyl group, or $R^1$ and $R^2$ together with the nitrogen atom to which they are attached form a group represented by the formula:

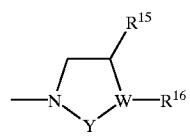

wherein W is CH, a carbon atom or a nitrogen atom, Y is a group of —C(=O) or —$(CH_2)_m$— wherein m is 1 or 2, $R^{15}$ and $R^{16}$ are each a hydrogen atom or when W is a 5 carbon atom, $R^{15}$ and $R^{16}$ together with the carbon atoms to which they are attached form a benzene ring or a naphthalene ring, $R^3$ is a hydrogen atom, an alkyl group having 1 to 5 carbon atoms or a cinnamyl group, $R^4$ is a hydrogen atom, an acetyl group, an ethylsuccinyl group or a nicotinoyl group, A is a group represented by the formula:

—OC(=O)—$R^{17}$,

—OC(=O)—$CH_2$—$R^{17}$,

—OC(=O)—NH—$R^{17}$,

—O—$R^{17}$ or

—OC(=O)—O—$R^{17}$ wherein $R^{17}$ is a phenyl group, a pyridyl group, a quinolyl group, or those groups which are each substituted by 1 to 3 members selected from the group consisting of an alkyl group having 1 to 5 carbon atoms, a nitro group, an alkoxy group having 1 to 5 carbon atoms and a halogen atom, and $R^5$ and $R^6$ are each a hydrogen atom or an alkyl group having 1 to 5 carbon atoms or a pharmaceutically acceptable salt thereof.

2. A pharmaceutical composition comprising a pharmaceutically acceptable carrier and an effective amount of the erythromycin A derivative or a pharmaceutically acceptable salt thereof according to claim 1.

3. An antibacterial preparation comprising a pharmaceutically acceptable carrier and an effective amount of the erythromycin A derivative or the pharmaceutically acceptable salt thereof according to claim 1 as an effective component.

4. A method for the treatment of a bacterially infectious disease which comprises administering a pharmaceutically effective amount of the erythromycin A derivative or a pharmaceutically acceptable salt thereof according to claim 1 to a patient.

* * * * *

UNITED STATES PATENT AND TRADEMARK OFFICE
CERTIFICATE OF CORRECTION

PATENT NO.    : 6,191,118 B1
DATED         : February 20, 2001
INVENTOR(S)   : Asaka et al.

It is certified that error appears in the above-identified patent and that said Letters Patent is hereby corrected as shown below:

Title page,
Item [57], ABSTRACT,
Formula (I) which reads:

"
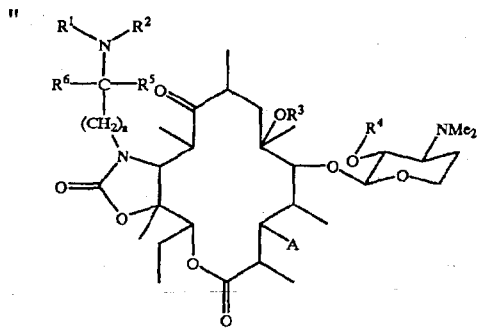
"

should read:

--
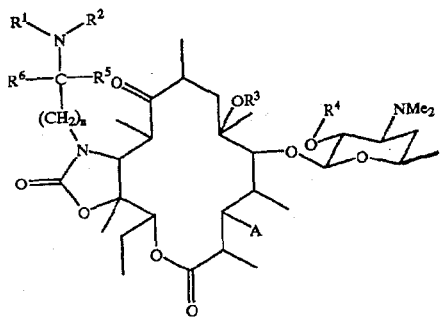
--.

UNITED STATES PATENT AND TRADEMARK OFFICE
CERTIFICATE OF CORRECTION

PATENT NO.   : 6,191,118 B1
DATED        : February 20, 2001
INVENTOR(S)  : Asaka et al.

It is certified that error appears in the above-identified patent and that said Letters Patent is hereby corrected as shown below:

Column 2,
Formula (I) which reads:

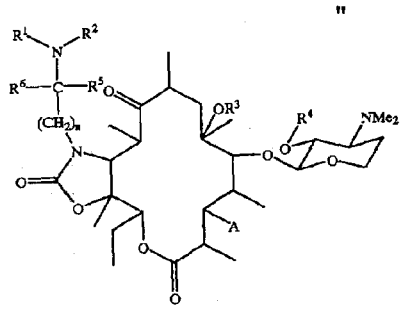

should read:

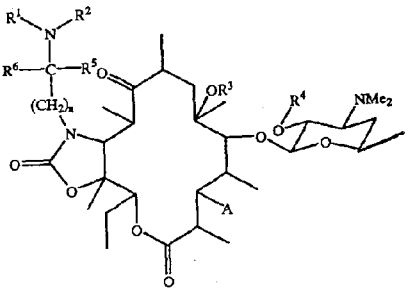

Column 3,
Line 38, "atoms]" should read -- atoms --.

Column 12,
Line 53, "imoles" should read -- mmoles --.

UNITED STATES PATENT AND TRADEMARK OFFICE
CERTIFICATE OF CORRECTION

PATENT NO. : 6,191,118 B1
DATED : February 20, 2001
INVENTOR(S) : Asaka et al.

It is certified that error appears in the above-identified patent and that said Letters Patent is hereby corrected as shown below:

Column 22,
Line 54, "turned" should read -- returned --; and
Line 58, "turn" should read -- returned --.

Column 23,
Line 16, "6-OCH$_3$" should read -- 6-OCH$_3$ --;
Line 18, (Q, 6-OCH$_3$)" should read -- (Q, 6-$\underline{O}$CH$_{\underline{3}}$) --;
Line 22, "deoxy-$^3$-" should read -- deoxy-3- --.

Column 25,
Line 19, "dimethylaminoenzaldehyde" should read -- dimethylaminobenzaldehyde --;
Line 30, "0.329" should read -- 0.32g --.

Column 27,
Line 2, "nmole" should read -- mmole --;
Line 34, "%3" should read -- %, --.

Column 28,
Line 44, "–COCH$_3$)" should read -- –COCH$_{\underline{3}}$) --;
Line 45, "N(CH$_3$)$_2$)," should read -- N(C$\underline{H}$$_3$)$_2$), --;
Line 57, "–COCH$_3$" should read -- –COCH$_{\underline{3}}$) --; and
Line 58, N(CH$_3$)$_2$)," should read -- N(C$\underline{H}$$_3$)$_2$), --.

Column 29,
Line 20, "$_{60}$º" should read -- 60º --;
Line 22, "$_[$3-Pyr.]" should read -- [3-Pyr.] --;
Line 23, –NCH$_2$" should read -- –N(C$\underline{H}$$_2$ --;
Line 25, "$_{60}$º" should read -- 60º --;
Line 26, N(CH$_3$)$_2$)" should read -- (N(C$\underline{H}$$_3$)$_2$) -- and "(–NCH$_2$[3-" should read -- (–NC$\underline{H}$$_2$[3- --;
Line 28, "COCH$_2$" should read -- $\underline{C}$OCH$_2$ --;
Line 46, "(N(CH$_3$)$_2$)" should read -- N(C$\underline{H}$$_3$)$_2$) --;
Line 49, "(N(CH$_3$)$_2$)" should read -- N(C$\underline{H}$$_3$)$_2$) --;
Line 51, "COCH$_2$" should read -- $\underline{C}$OCH$_2$ --; and
Line 65, "E" should read -- H --.

UNITED STATES PATENT AND TRADEMARK OFFICE
CERTIFICATE OF CORRECTION

PATENT NO. : 6,191,118 B1
DATED : February 20, 2001
INVENTOR(S) : Asaka et al.

It is certified that error appears in the above-identified patent and that said Letters Patent is hereby corrected as shown below:

<u>Column 30,</u>
Line 13, "9" should read -- g --.

<u>Column 31,</u>
Line 22, begin a new paragraph with "$^{13}$C-NMR"; and
Line 51, begin a new paragraph with "$^{13}$C-NMR".

<u>Column 32,</u>
Line 17, "imole" should read -- mmole --;
Line 37, begin a new paragraph with "$^{13}$C-";
Line 53, begin a new paragraph with "$^{13}$C-".

<u>Column 33,</u>
Line 3, begin a new paragraph with "$^{13}$C-";
Line 20, begin a new paragraph with "$^{13}$C-NMR"; and
Line 36, begin a new paragraph with "$^{13}$C-".

<u>Column 36,</u>
Line 22, begin a new paragraph with "$^{13}$C-NMR".

<u>Column 37,</u>
Line 48, "Q." should read -- Q, --.

<u>Column 40,</u>
Line 20, "—C(==O)" should read -- –C(=O)- --.

Signed and Sealed this

Twenty-seventh Day of August, 2002

*Attest:*

JAMES E. ROGAN
*Attesting Officer*   *Director of the United States Patent and Trademark Office*